(12) United States Patent
Stray-Gundersen et al.

(10) Patent No.: US 11,207,237 B2
(45) Date of Patent: Dec. 28, 2021

(54) EFFICACY BASED FEEDBACK SYSTEM FOR BLOOD FLOW RESTRICTION TRAINING

(71) Applicants: James Stray-Gundersen, Park City, UT (US); Sean Tremaine Whalen, Tallinn (EE)

(72) Inventors: James Stray-Gundersen, Park City, UT (US); Sean Tremaine Whalen, Tallinn (EE)

(*) Notice: Subject to any disclaimer, the term of this patent is extended or adjusted under 35 U.S.C. 154(b) by 79 days.

(21) Appl. No.: 16/741,730

(22) Filed: Jan. 13, 2020

(65) Prior Publication Data
US 2020/0352819 A1    Nov. 12, 2020

Related U.S. Application Data

(63) Continuation of application No. 15/653,429, filed on Jul. 18, 2017, now abandoned.

(60) Provisional application No. 62/363,854, filed on Jul. 19, 2016.

(51) Int. Cl.
| | |
|---|---|
| *A61H 9/00* | (2006.01) |
| *A61H 11/00* | (2006.01) |
| *A63B 21/008* | (2006.01) |
| *A63B 21/00* | (2006.01) |
| *A63B 23/12* | (2006.01) |

(52) U.S. Cl.
CPC ......... *A61H 9/0092* (2013.01); *A61H 9/0085* (2013.01); *A61H 11/00* (2013.01); *A63B 21/0085* (2013.01); *A63B 21/4025* (2015.10); *A63B 23/12* (2013.01)

(58) Field of Classification Search
CPC .... A61H 9/0092; A61H 9/0085; A61H 11/00; A61H 9/0078; A61H 2011/005; A63B 21/4025; A63B 23/12
See application file for complete search history.

(56) References Cited

U.S. PATENT DOCUMENTS

| | | | |
|---|---|---|---|
| 8,021,283 B2* | 9/2011 | Sato ....................... | A63B 24/00 482/111 |
| 8,182,403 B2* | 5/2012 | Sato ................... | A63B 21/4025 482/113 |
| 8,328,693 B2* | 12/2012 | Sato ................. | A63B 21/00076 482/4 |
| 2010/0279820 A1* | 11/2010 | Sato ................... | A63B 21/0023 482/4 |

(Continued)

*Primary Examiner* — Steven O Douglas
(74) *Attorney, Agent, or Firm* — Snell & Wilmer L.L.P.

(57) ABSTRACT

An inflatable belt 100 for use in a BFR system with an outer belt material 102 hermetically sealed to an inner belt material 101 along a perimeter, thereby forming at least one inflatable chamber 103, the inflatable chamber having an input port 104 for accepting a gas into the chamber, the inflatable belt further comprising a first fastening means 110 in communication with the outer belt material, for attaching to a second fastening means 111 in communication with the outer belt material, thereby locking a circumference of the inflatable belt, when wrapped around a user's limb, efficacy feedback means 200 for gathering efficacy feedback data 205, for use in prescribing, monitoring and adjusting one or more training parameters of a BFR training session and/or program based on evaluation of the efficacy feedback data.

19 Claims, 6 Drawing Sheets

(56) References Cited

U.S. PATENT DOCUMENTS

Figure 1:
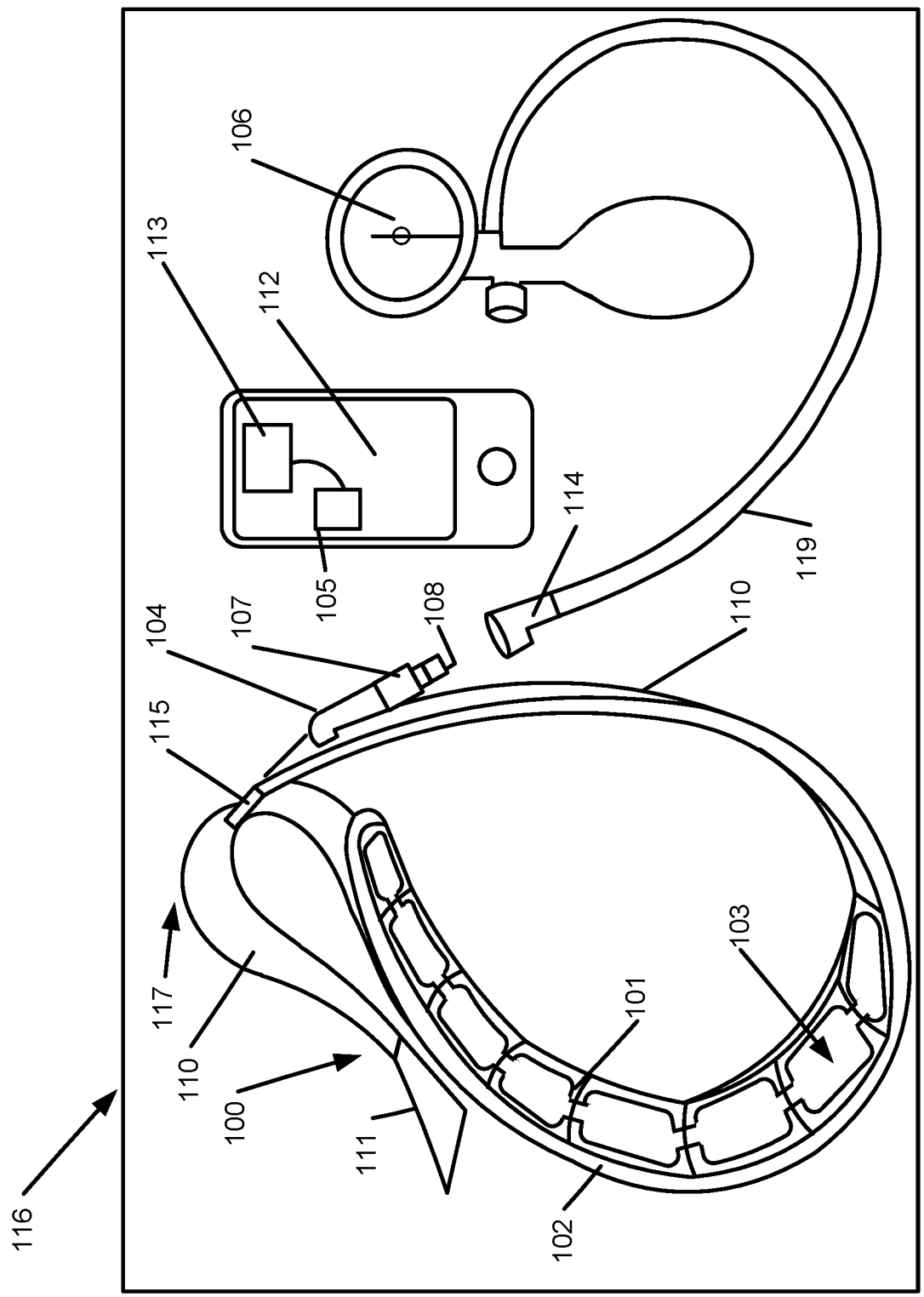

| | | | | |
|---|---|---|---|---|
| 2010/0324429 A1* | 12/2010 | Leschinsky | .......... | A61B 17/135 600/493 |
| 2015/0150560 A1* | 6/2015 | Sato | .................... | A61H 9/0092 606/202 |
| 2017/0112504 A1* | 4/2017 | McEwen | ............ | A63B 21/4025 |
| 2017/0312165 A1* | 11/2017 | Johnson | ................. | A41D 1/005 |

* cited by examiner

FIG 3B

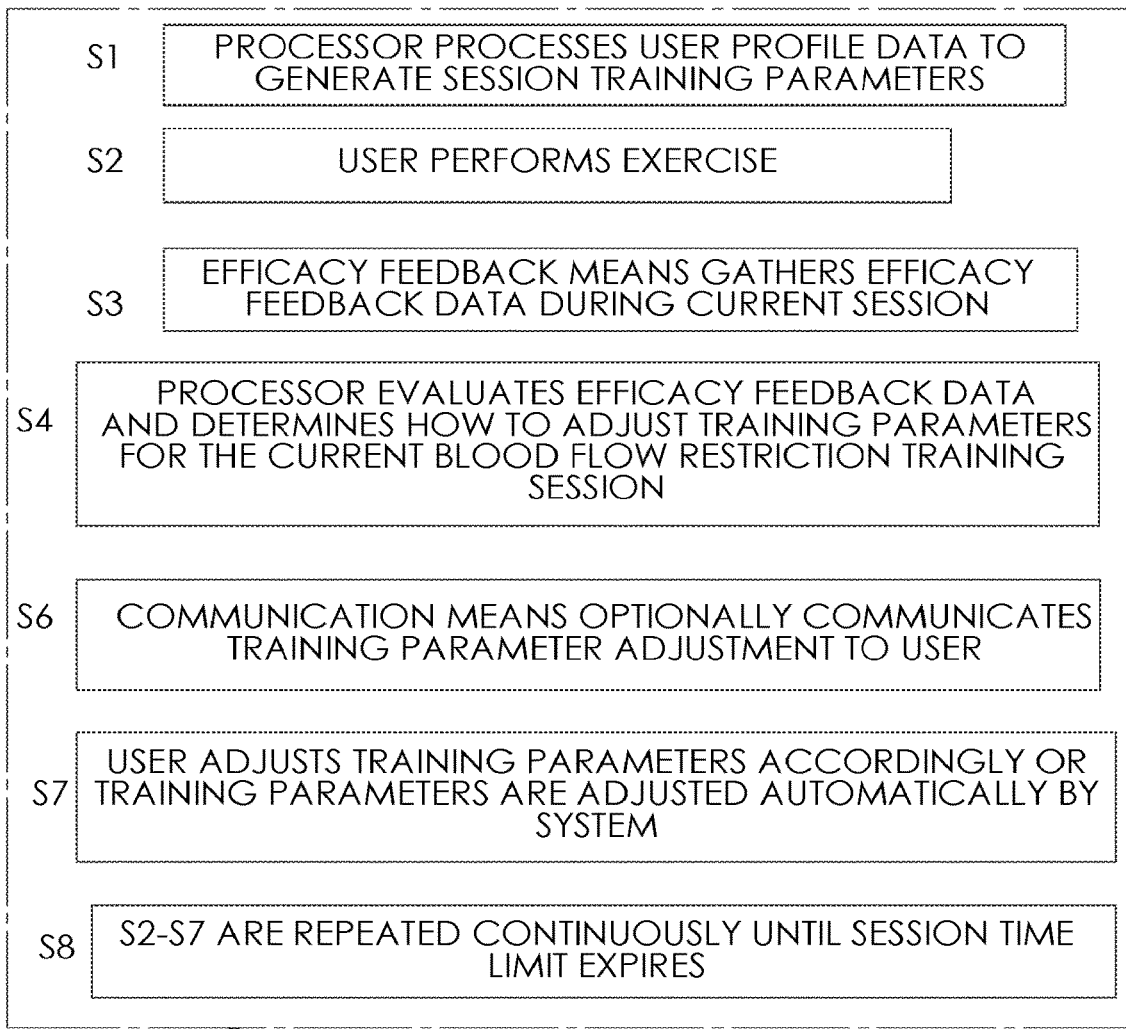

| S1 | PROCESSOR PROCESSES USER PROFILE DATA TO GENERATE SESSION TRAINING PARAMETERS |
| S2 | USER PERFORMS EXERCISE |
| S3 | EFFICACY FEEDBACK MEANS GATHERS EFFICACY FEEDBACK DATA DURING CURRENT SESSION |
| S4 | PROCESSOR EVALUATES EFFICACY FEEDBACK DATA AND DETERMINES HOW TO ADJUST TRAINING PARAMETERS FOR THE CURRENT BLOOD FLOW RESTRICTION TRAINING SESSION |
| S6 | COMMUNICATION MEANS OPTIONALLY COMMUNICATES TRAINING PARAMETER ADJUSTMENT TO USER |
| S7 | USER ADJUSTS TRAINING PARAMETERS ACCORDINGLY OR TRAINING PARAMETERS ARE ADJUSTED AUTOMATICALLY BY SYSTEM |
| S8 | S2-S7 ARE REPEATED CONTINUOUSLY UNTIL SESSION TIME LIMIT EXPIRES |

301

THIS IS REALLY JUST AN EXPANSION IN FUNCTIONALITY ON S10 FROM FIG3A

THIS IS REALLY JUST AN EXPANSION IN FUNCTIONALITY ON S10 FROM FIG3A

EFFICACY BASED FEEDBACK SYSTEM FOR BLOOD FLOW RESTRICTION TRAINING

CROSS-REFERENCES TO RELATED APPLICATIONS

This application is a continuation of Ser. No. 15/653,429, filed Jul. 18, 2017 entitled EFFICACY BASED FEEDBACK SYSTEM FOR BLOOD FLOW RESTRICTION TRAINING which claims priority to provisional application 62/363,854, filed on Jul. 19, 2016, entitled Efficacy Based Feedback System for Blood Flow Restriction Training. This application also references in their entirety the previously filed provisional patent applications numbered 62/293,536, filed on Feb. 10, 2016, titled Blood Flow Restriction Belts and System by Whalen, and 62/311,936, filed on Mar. 23, 2016, titled Barrel Inflatable Belt by Whalen. Some of the concepts herein were disclosed in 62/293,536 and 62/311,936 and the authors, in this application, wish to elaborate on those concepts as well as introduce new inventions.

FEDERALLY SPONSORED RESEARCH

Not Applicable

SEQUENCE LISTING OR PROGRAM

Not Applicable

FIELD OF THE INVENTION

This invention relates to blood flow restriction systems, and more specifically to an individualized blood flow restriction monitoring system for continuously monitoring and prescribing a blood flow restriction training program that is optimally safe and effective for each individual user without the need for a specialist, trainer, or intervention from another individual.

BACKGROUND OF THE INVENTION

Blood Flow Restriction Training (BFR) is spreading globally. However, there are various aspects of current technology and expertise that are limiting the distribution of the technology. The BFR training system, and method described in these applications is a distinctive non-conventional one that involves compression of an arm and/or leg at a position near the top thereof.

A relatively narrow (4-10 centimeter), pneumatic belt of unique design, is applied at a proximal location on an extremity, proximal to the main belly of the m. bicep brachia on the arm, and as high on the thigh, as possible, on the leg. The desired effect is to produce an obstruction or impediment to deep venous flow coming out of the limb. To the extent possible, veins and capillaries in the distal muscle are distended and full of blood. The muscle belly and its blood vessels are not covered by the belt, allowing some blood to perfuse those fibers.

Once in place, the belt is inflated to a certain pressure to alter the circulation in the vasculature of the extremity, and this particular pressure level is critical for the effectiveness of this BFR technique.

Effects on the Vasculature.
a. Superficial Veins—are completely blocked by the inflated belt, resulting in distended surface veins and redirecting blood into the deep venous system.
b. Deep Veins—Change the pattern of the deep venous outflow from a rhythmic, gentle steady stream of blood, flowing back to the central circulation, to a more pulsatile flow ranging from no flow (0 mls/sec) at times, to very brisk flows (>100 mls/sec) with distal muscular contractions. The deep venous system distends to accommodate the flow into the extremity that is temporarily prevented or impeded from leaving the extremity and then collapses as blood is emptied by muscle contraction and pushed past the deep venous obstruction.
c. The Capillary network is distended and has increased permeability.
d. Arteries—may have inflow reduced, but remain patent.
e. Arterioles—which are the main control of vascular resistance, distal to the band are fully dilated.

At high belt pressures, deep veins are temporarily obstructed until muscle contraction moves blood in the deep veins out of the extremity. When that happens, blood from the arterial side fills back into the extremity. Under these circumstances arterial inflow waxes and wanes depending on the frequency of muscle contraction emptying the deep veins, making more room for fresh, oxygenated, arterial blood. At lower pressures, arterial inflow is not reduced at all, but at higher and higher pressures, due to the inability to overcome the deep venous obstruction and the pressure itself, arterial inflow is reduced, but not eliminated.

Changes in the Circulation have the Following Effects:
1. By Impeding and modulating blood flow in a certain manner causes;
    i. Angiogenesis—Due to the effects on the vasculature, NO release, the distension of the capillaries and veins and periodic flushing and emptying of the deep veins, all work to stimulate release of an angiogenic cascade documented by increases in circulating VEGF, and mRNA for various angiogenic factors.
    ii. This reduced and modulated blood flow is inadequate to recover the active muscle from otherwise easy, sustainable efforts. A Disturbance of Homeostasis in Active Muscle (primarily, consisting of a decrease pH, decrease pO2, increased lactate concentrations and deplete intracellular phosphates ATP/CP, increase concentrations of Pi, ADP and AMP, altered electrolyte concentrations) ensues as the initial fibers recruited are unable to maintain their work rate.
    iii. This Disturbance of Homeostasis causes initially recruited fibers (primarily fatigue resistant, type I fibers) to fail to produce the necessary force, so that additional larger motor units (with more easily fatigable Type II fibers) are recruited to perform the work. In turn, these Type II fibers become quickly fatigued as their pH and pO2 decrease and their intracellular phosphate stores are depleted and are unable to be replenished.
2. Metabolites from the Disturbance of Homeostasis, accompanied by an anabolic hormonal milieu, stimulate an increase in local protein synthesis in all motor units that were recruited and contracted, via the mTOR pathway.
3. The Disturbance of Homeostasis is also communicated via unmyelinated Group III and IV afferent fibers connected to metaboreceptors and nociceptors, to the CNS and is perceived as "burning", "fatigue", or "discomfort" in the active muscle. The CNS also, increases sympathetic tone and releases an anabolic hormone cascade as noted by a robust increase in circulating growth hormone (GH). The increase in sympathetic tone, increases ventilation and heart rate. The GH release initiates an anabolic cascade, resulting in IGF-1. The anabolic hormone cascade also binds to anabolic cell surface receptors that have been up-regulated in active tissues, facilitating the local stimulation of increasing protein synthesis.

Estimating Excess Post-Exercise Oxygen Consumption (EPOC) from Heart Rate and Heart Rate Variability (R-R') Data Collected During Exercise.

Training Load Assessment

It is difficult to select an optimal exercise dose. Sufficiently strenuous exercise causes a disturbance in body's homeostasis which after recovery results in improved fitness (E.g. Brooks & Fahey 1984; Åstrand & Rodahl 1986). Too easy training does not improve fitness but too hard training may in long term lead to overtraining. It is therefore important to measure the training load. In addition, BFR further complicates finding the correct exercise dose due to creation of a disturbance of homeostasis via restriction of blood flow, which decreases $pO_2$ and pH in active muscle, rather than the normal indicators of fatigue such as glycogen depletion or micro trauma to the contractile apparatus or altered electrolyte gradients.

Methods that are used in assessing training load may be broadly characterized as subjective and physiological measures. Subjective measures are easy to access, but do not always reflect physiological responses and recovery demand. Traditional physiological measures, such as oxygen consumption ($VO_2$), heart rate and blood lactate, reflect mainly momentary intensity of exercise and not length of exercise or cumulative exercise load. There are also training load measures such as training impulse (TRIMP), but which does not have physiological basis or scale and therefore may be difficult to interpret.

EPOC is a physiological measure (amount of oxygen consumed in excess after exercise as measured in liters or ml/kg) that that reflects the recovery demand and the disturbance of body's homeostasis brought by the exercise. Measurement of EPOC has been possible only by analyzing respiratory gases with laboratory equipment, thus being expensive, time consuming and not applicable to everyday purposes.

The lack of valid and easy-to-apply physiology based method for the assessment of training load has led to development of a method to estimate EPOC indirectly from R-R' measurements.

EPOC in Exercise Sciences

The first observation of an elevated resting metabolic rate after exercise was made in 1910 by Benedict and Carpenter and was later studied as "oxygen debt" (Hill and Lupton in 1923). The present name EPOC has been used not only to represent oxygen repayment during recovery but also to reflect the general exercise-induced disturbance of body's resting metabolism (Gaesser & Brooks 1984; Gore & Withers 1990) and resting homeostasis (Brehm & Gutin 1986): "the cause of Excessive Post-Exercise Oxygen Consumption (EPOC) is the general disturbance to homeostasis brought on by exercise" (Brooks & Fahey 1984).

EPOC reflects the body's recovery requirements after exercise. Active oxygen-consuming recovery processes occurring in the body are due to replenishment of body's resources ($O_2$-stores, ATP, CP) and increased metabolic rate (increased HR and respiratory work, elevated body temperature) caused by metabolic by-products and hormones produced during exercise. (Brooks & Fahey 1984; Åstrand & Rodahl 1986; Børsheim & Bahr 2003)

EPOC reflects a general disturbance in body's homeostasis caused by exercise.

EPOC is calculated by subtracting the area under resting $VO_2$ from the area under the recovery $VO_2$ curve EPOC gets higher with higher intensity and/or longer duration of exercise (e.g. Børsheim & Bahr 2003)

Indirect EPOC Prediction Method Based on Heart Rate Measurement.

The EPOC model was constructed based on meta-analysis data of peer-reviewed articles. Only valid studies were carefully selected for this purpose. The data included 48 different exercise settings, including a total of 158 trained and untrained male and female subjects. Exercise durations ranged from 2 to 180 minutes and exercise intensities from 18 to 108% of $VO_{2max}$. The modeling data included both continuous and intermittent exercises and consisted of running, cycling and upper-body ergometer exercise.

EPOC is predicted only on the basis of R-R' derived information. The variables used in the estimation are current intensity (% $VO_{2max}$) and duration of exercise (time between two sampling points, $\Delta t$) and EPOC in the previous sampling point. The model is able to predict the amount of EPOC at any given moment. No post-exercise measurement is needed. The model can be mathematically described as follows:

$$EPOC_{(t)} = f(EPOC_{(t-1)}, exercise\_intensity_{(t)}, \Delta t). \quad (1) \text{ (Saalasti 2003)}$$

At low exercise intensity (<30-40% $VO_{2max}$), EPOC does not accumulate significantly after the initial increase at the beginning of exercise. At higher exercise intensities (>50% $VO_{2max}$), EPOC accumulates continuously. The slope of accumulation gets steeper with increasing intensity. With BFR, we attempt to create a disturbance of homeostasis that will reflexely cause the R-R' interval to show variation consistent with high intensity work, thus, we have a marker of appropriate intensity for BFR by examining the slope of the EPOC accumulation. A flat slope indicates little disturbance in homeostasis, while a steep positive slope indicates a great disturbance of homeostasis. Normally, one would need to proceed with caution when encountering a steep positive accumulation of EPOC, but with BFR, we have created the disturbance by restricting blood flow as opposed to micro trauma or glycogen depletion, thus, when normal blood flow is restored, the exercising tissues recover quickly, since there is little micro trauma to repair. In this way, we are uniquely tapping into the body's "warning systems" to monitor and titrate the exercise dose. Because we have elicited the "warnings" by blood flow restriction, and not done significant damage, the body recovers quickly and builds new and better tissues rapidly.

Exercise Choice and Protocol

What prior art devices fail to address is that there are many variables that must be tuned correctly in order to achieve results: initial belt tension, pressure in the belt (in the case of pneumatic belts), weight used or load applied, number of reps and type of exercise, rest period between sets, number of sets, number of exercises, etc. The reader shall note that the applicants' suggested protocol is but one example and there are numerous suggested protocols in the art, and the applicants' invention shall not be limited to any specific protocol recommendation. The applicants' invention is a feedback system concept that may be used in conjunction with many different protocols. Other devices are focused on safety and setting up the initial settings such as to avoid full occlusion, however this leaves the user unsure of whether those settings are effective. For example, a user may have a pressure set correctly or optimally at the outset, but may not be using enough load during the exercises. Because the general prescription in prior art devices is "light loads", which is inherently non-specific, the user is left to guess whether a session produced results with the load they selected. Further, the problem of not having efficacy feedback is exacerbated by the fact that the BFR training methodology is so new that most users are unsure what they should experience or how they can recognize an effective session. Therefore, there is a need of an invention such as the applicants', to provide a measurable result to inform a user that they did BFR training correctly, or make suggestions on what to change either during a session or for a subsequent session in order to get the right result.

There is good reason for the specific protocol of exercises to make the BFR session efficacious. The applicants recommend a series of exercises that utilize all muscle groups distal the belt, as well as, muscle groups proximal to the belt. For example this could be a sequence of 3 sets of 30 repetitions separated by 30 second "rest" periods for each exercise. Typically, the person can perform the first 30 repetitions with minimal feelings of fatigue or only during the last few repetitions. Then there is a 30 second "rest" period where, if properly adjusted, the circulation slows down even more since venous blood does not have the force of muscle contraction to pump blood back into the central circulation and blood flow slows considerably and may stop. This further reduces the ability of the muscle to recover and normalize pO2 and pH. The intracellular muscle fiber milieu deteriorates as homeostatic conditions are lost. Then the second set of exercise commences. On one hand the circulation is improved, but the exercise is now being carried out by fibers with little O2, a low pH and a disturbed milieu. Contraction in those initial fibers fails, now other motor units must be recruited to produce the necessary force. Their milieu is disturbed even sooner and this disturbance of homeostasis is being communicated to the CNS. Another 30 second "rest" period ensues where the circulation is further reduced and cellular milieu of active motor units, further deteriorates. Now a third set of repetitions is performed utilizing fibers with very disturbed homeostasis. Failure of contraction happens quickly. Other motor units in the muscle are recruited to produce the necessary force and they begin to fail, partially because the low pO2 and low pH produced by initial motor units diffuses into the later recruited fibers, and partially, because these fibers are rarely recruited and are very glycolytic, rapidly contributing to a milieu inhibiting muscle contraction. Contraction failure of virtually all motor units in the muscle ensues. A robust signal of "failure" is sent to the CNS and the CNS reacts by secretion of an anabolic hormonal cascade.

Taken together, when one performs relatively easy exercise with muscles that have restricted, inadequate blood flow to sustain the work, a disturbance of homeostasis in the muscle ensues, prompting recruitment of additional fibers and ultimately resulting in muscle contraction failure. This "failure of contraction" stimulates local protein synthesis for repair and adaptation, as well as, initiating a systemic response from the CNS to repair and adapt working tissues.

Since the absolute workloads are light, they caused minimal damage to working muscle and much less damage than is normally associated with muscle contraction failure, thus, improvement in function occurs more rapidly than when damage must first be repaired.

"Failure of Contraction" in the applicant's system definition, occurs when the motion (e.g. elbow flexion) cannot be done anymore, but it may also be recognized when the "form" of the exercise is altered or deteriorates (indicating accessory muscles taking over the load) or if the frequency of the repetitions slows down. Both altered form and a decrease in frequency of repetitions can be documented by alterations in an accelerometer signal or other similar motion capturing sensor, such as a camera or reflector balls and 3D camera system. An indication of the Disturbance of Homeostasis and its communication to the CNS, is the increase in sympathetic tone, causing an increase in heart rate and ventilation over and above the response to the same exercise without blood flow restriction. This increase in sympathetic tone can be detected by a change in heart rate variability (HRV) indicies.

It should be noted that there is no conclusive consensus in the scientific community currently as to what the precise mechanisms are behind the effects of BFR training. The applicants contend that effective BFR training is associated with, but not limited to, degradation of the muscle fiber milieu, "failure" of contraction (identified by an accelerometer) and the transmission of the "distress" signal to the CNS. The failure can be noted by, but not limited to, changing the form of the exercise or decreasing the frequency of the repetitions. The transmission of the "failure signal" to the CNS can be noted by, but not limited to, and not exclusively, a relatively greater increase in heart rate and ventilation due to increased sympathetic tone. This increase in sympathetic tone can be objectively documented by, for example, but not limited to, a decrease in heart rate variability, noted by various indicies.

While studies in the literature have shown that BFR is effective at building muscle strength over a period of weeks, no study or piece of information that the author could find discusses looking how to know if a single session was effective, or the degree to which it was effective. There is similarly no discussion of how to adjust parameters of a BFR training session during the session. Further, there is no objective guidance as to how to find or adjust appropriate tensions or pressures for effective use. In today's age where instant gratification is at one's fingertips for just about everything, having some feedback as to whether a session was effective is important to keep users motivated to continue what is probably, for most, a new form of training. Further, Sato has been exclusively focused on the safety aspects of BFR and ensuring that pressures and/or tensions used in his studies, or equipment and sensors monitoring blood flow etc, keep someone in a safe operating zone. However, Sato does not discuss how to tell whether a session is effective or not, just mentioning that over a long period of time the method and equipment demonstrate strength gains. Sato, and KAATSU Global teach a setup method involving checking capillary refill times in order to determine whether a pressure is appropriate, however this doesn't address effectiveness of the session as the user may not be well versed at how to measure this, and the measurement is in and of itself subjective. Sato fails to teach the most important aspect of the training session which is measuring whether a session was effective. Similarly in the research, the researchers typically use a standard 160 mmHg as the pressure for every subject. But in reality, a the authors have gleaned from practical experience, the appropriate pressures are highly depending on belt design, and different for every person and depend on the hardware being used, how long they have been doing BFR training, and other factors like how tightly the belts are applied initially. To illustrate this, the researchers use wide cuffs when showing that 160 mmHg occludes flow for most subjects, and the applicant has done experiments to show that with the applicant's belts, 160 mmHg would be completely ineffective because of the width of the applicant's belts are inadequate to provide sufficient restriction on certain individuals at those pressures. So currently, there is a broad lack of guidance as to how to set, adjust, and fine tune the appropriate pressure, weights used, and tension settings for BFR training other than with safety in mind. The applicants further contend that the most effective way to perform and guide BFR training is by looking at the efficacy of each session and adjusting the pressures in a continuous feedback loop from one session to the next. This gives the most frequent amount of updating and adjustment to get the pressures quickly into the right spot for effective training sessions. Sato teaches only to look at pressures for a given session via the capillary refill check without regard to prior history. This necessitates a cumbersome setup process before each session without actually guaranteeing the session will be effective. The reader shall note that while the applicants generally discuss the concept of pressure and pneumatic belts, the same can easily apply to tension levels in non-pneumatic belts. Evaluating the efficacy of a session will decrease the number of sessions needed to reach results and improve the overall training program experience. The applicant has discovered a number of ways to measure and document efficacy, including, but not limited to:

1. Subjective feelings of fatigue/"burn" in working muscle.
2. Deterioration in the technical form of the exercise, calling on accessory muscles to perform the movement.
3. Reduced frequency of contractions. Slowing down the rate of repetitions.
4. Increase in sympathetic tone shown by an elevated heart rate, ventilation and sweating, above what would be expected for the exercise alone, or above a baseline session
5. Failure to complete a required number of repetitions, for example, 30 repetitions, in each set, e.g. 30-25-16 reps in the 3 sets.
6. Measuring the overall time duration of a BFR training session, and optionally the time duration of each set of repetitions.

As one example, by collecting R-R' and accelerometer data, one can objectively document an effective session, which can be used instead of subjective feelings or in addition to the subjective markers.

While previously filed applications describe the general concepts involved hi BFR training and document the gains in strength, they do not address accurately what is happening to a user physiologically, and specifically, how these changes and signals produced and felt by the user's body can be used to guide future sessions. Much regard is paid to the concept of safety, and the risks associated with BFR training, and inventions are previously disclosed around how to monitor for safety concerns and effect equipment function based on those monitoring results. As described above, the inaccuracy of understanding of what is happening in the body inherently makes it clear that the inventors don't understand how efficacy can be evaluated and tied into a feedback loop, as the applicant describes herein, to make effective user-specific pressures or tensions prescriptive, and not a variable left to a judgement call by an inexperienced user or other trainer.

However, no attention is paid to the concept of monitoring the efficacy of such training. As BFR is a novel training method that majority of people have never experienced, most people don't have an idea what it should feel like, or how to know if it is working, or how to set appropriate levels of restriction, etc. Sato generally describes the need for an expert, certified trainer or medical specialist to properly and safely implement BFR training, but this significantly limits the potential for adoption and excludes individual consumers from using the product for themselves. Further, Sato focuses heavily on monitoring of pressures, heart pulse rate and other measures aimed at safety, but does not address how to ensure a training program is effective. This oversight leaves a major component of a complete system unserved and as the applicant will describe, monitoring the efficacy in combination with the inventions from the applicant's prior applications referenced herein, and new inventions on methodology of how to prescribe initial pressures, can actually make all the safety monitoring inventions and requirements proposed by Sato, obsolete. Further, when combined with benchmarking to measure progress over time, the applicants' invention gives users a complete turnkey package with which to start BFR training.

As the applicant will describe, a monitoring system that initiates the BFR training program at a safe level, monitors efficacy without the need for a third party, and guides a user automatically through their program offers a significant usability advantage over current systems that require a specialist or trainer to guide an individual, and make the need for complex and expensive safety monitoring obsolete. It is also very useful to trainers though because a trainer can remotely monitor whether their clients are doing the exercise properly. By knowing whether their clients are having effective sessions, trainers can provide feedback and better quality of service to their clientele.

Various patent applications by two inventors, Sato and Wasowski, have been issued on the devices, apparatus, and methods used to implement BFR training, and various other methods have been published in research papers as discussed. It will be shown how there are yet many improvements to be made both on the apparatus, system and method of application to promote widespread adoption, in the areas of cost effectiveness, comfort, and ease of use. Both inventors describe in their applications the importance of reducing the cost of the system (Sato U.S. Pat. No. 8,992,397), improving the comfort level (Wasowski U.S. Pat. No. 8,273, 114), and making the system easy and safe to use, together with an instructor or by oneself (Sato U.S. Pat. No. 8,992, 397), as the principal barriers to mass adoption, and it is the aim of the applicant to solve these deficiencies in existing products and disclosed embodiments.

U.S. Pat. No. 8,273,114

U.S. Pat. No. 8,273,114 to Wosowski describes a full body suit with the addition of cooling, electrical grounding, and a variety of other features. Wosowski's invention appears to be a variation of Sato's designs, but is significantly more costly and difficult to use. Further Wosowski does not go into any detail on the blood flow restriction means other than to say they are like ordinary blood pressure cuffs. Wosowski describes monitoring pulse to look for signals that are too weak as a safety mechanism but doesn't address at all the concept of how to adjust pressures for efficacy. Indeed no mention of any kind of feedback mechanism is present in Wosowksi's application.

U.S. Pat. Nos. 6,149,618 & 7,413,527 & 7,455,630

U.S. Pat. Nos. 6,149,618 and 7,413,527 to Sato describe the methodology and theory behind blood flow restriction training, or KAATSU TRAINING™, as Sato calls it. Sato demonstrates through studies and publications that the treatment is effective but doesn't describe at all how the tensions were chosen or any kind of feedback mechanism employed by the product or system to achieve those results, which leaves a large void in the product and system offering as it is totally unclear to a user how to use and adjust the product.

In fact current KAATSU methodology includes checking capillary refill times, and what amounts to a judgement call by the user of what the right refill time is, or in the case of darkly pigmented users, is actually virtually impossible to do. The applicant's system and methodology remove any type of judgement calls from the user, while maintaining a system that is safe, effective, and prescriptive.

U.S. Pat. No. 7,413,527 to Sato introduces the concept of an inflatable bladder but again makes no mention of how a user is to determine what pressures to inflate to, and no mention of feedback for the user to know how to adjust pressure. Sato claims the method is effective, but it can be clear to the examiner that if the bands are placed extremely loosely on the user, they may inflate to fill the chamber volume, and reach their elastic limit before putting any meaningful compression on the limb, and it will be like the belts are not even present.

U.S. Pat. Nos. 8,021,283 & 8,328,693

Realizing the difficulty in facilitating widespread adoption based on the requirement for a trainer implementing the method to have significant expertise and knowledge of the body, Sato further continued to invent along the lines of automation and sensing to make KAATSU Training safe for any person. U.S. Pat. Nos. 8,021,283 and 8,328,693 to Sato principally focus on these automation aspects, and in particular safety monitoring aspects, assuming band designs as discussed prior. For example Sato mentions the need to monitor that a) heart rate doesn't exceed a maximum value b) blood pressure doesn't exceed a maximum value and c) pulsation rates are never abnormal. But Sato still fails to address how to determine if pressures lead to effective training, and how to create a system that will guide an individual through the training program and automatically adjust based on efficacy. Further, by myopically focusing on safety, as evidenced further by Sato's desire to monitor and maintain a constant pressure during the session (Sato discusses the inadequacy of just measuring bladder air pressure at the beginning of a training session because of physiological changes during the workout, for example the increase in limb circumference from doing work during KAATSU Training), Sato fails to realize that what happens during the session is not important as long as it is inherently safe, and that what really matters is knowing if the training was effective or not. I.e. a training session that was not effective and did not produce required fatigue is inherently safe. Sato's system includes a quantification target related to a state of blood flow that, in turn, dictates how much pressure is in the system, but again this is unnecessary and adds cost, and in the end is irrelevant because what determines whether the quantification target is correct in the first place is the result of the session as the applicant has described above. Finally, Sato mentions monitoring state of blood flow distal to the bands because he is looking to quantify the amount of restriction in the limb. The applicants contend that it doesn't matter what the level of restriction is in the arm (if it is known to be safe) as long as it produces an effective outcome, and therefore all the monitoring and extra equipment in Sato's product is unnecessary.

Sato mentions heart rate monitoring distal to the band, but this is different than the applicants' suggestion of monitoring heart rate variability which is a different parameter that indicates different things entirely; for example the applicants' invention does not even need to know the value of the heart rate to function. Further, to get heart rate variability it requires leads on either side of the heart for accuracy and therefore, by Sato limiting placement of his sensing devices, shows he is not considering HRV as an important parameter to monitor. Therefore Sato spends a lot of time describing a costly automated adjusting and monitoring product for safety reasons that is essentially made obsolete by the applicant's system in combination with belt design described in referenced provisional applications.

U.S. Pat. No. 8,328,693 to Sato further focuses on safety mechanisms and monitoring and doesn't address the efficacy monitoring at all. Sato again mentions heart beat rate, pulse wave data, and oxygen data characterized in the limb that is being restricted, but fails to note anything about heart rate variability, which requires sensors in other locations on the body, and reinforces this several times by associating heart beat rate measurements with occlusion determination. Sato even brings up the deficiency of heart beat rate in that it increases as the user exercises so determining a baseline and acceptable delta from the base as to what is unsafe vs. normal may not be possible. By focusing on the rate (beats per minute) and not the variability, Sato demonstrates he is not knowledgeable about using HRV as the mechanism for determining efficacy of the training session.

U.S. Pat. No. 8,182,403 & US2015/0150560A1

Sato continues to improve and perfect his KAATSU Training method in U.S. Pat. No. 8,182,403 to Sato and pending application US2015/0150560A1. In U.S. Pat. No. 8,182,403 Sato mentions the idea of using physiologic data such as sex, age, personal history of using KAATSU, as well as whether arms or legs are being compressed, and systolic blood pressure of the person as parameters for determining the upper and lower peaks for his cycling pressure function. Sato fails however to mention anything about how to adjust and monitor the program over time, and it is left to assume that there is one suggested pressure to operate with and that is all. In practice though, it has been shown that required pressure to maintain efficacy, changes over time and it is not sufficient to guess a person's pressure and let that be. In fact, KAATSU's regimen teach looking at timed capillary refill as a mechanism for determined the appropriate restriction pressure for a training program, but again, this is subjective. Sato's patent actually refers only to a cycling functionality which Sato classifies as equivalent to a warmup and then for use in normal training mode, and does not mention how the actual training restriction pressure should be determined, or adjusted over time. Sato's suggests that a definitive pressure can be found for the subject by giving an example of a healthy person and elderly person and not mentioning how the pressures may change over time.

In US2015/0150560A1 Sato mentions the autonomic nervous system and how compression can increase the activity of the sympathetic nerves and the decompression can enhance the activity of the parasympathetic nerves, and the cycling and repetition can stabilize the nerves of the user. While this is an interesting observation, Sato makes no connection between the nervous system and how to measure efficacy based on the impact of the training to the nervous system. Sato further suggests that the cycling is required to have an effect on the nervous system, which is incorrect, as blood flow restriction training at constant pressure has the impact on the nervous system as previously described. Sato describes a method of blood vessel training by alternating pressures but again fails to mention how training sessions would evolve over time, just that by cycling the pressures, the vessels increase in elasticity.

US20110125036

In US20110125036 to Sato, Sato describes use of KAATSU with those with metabolic syndrome and how safety is a major factor. He describes a diagnostic mode requiring measuring of a pulse wave to determine a pressure that corresponds with a maximum pulse wave valve to set the upper limit of the training pressure. But this requires extra sensors and procedures for determining this pressure and again only has safety in mind and not efficacy, principally assumed because of the nature of the population with metabolic syndrome. Sato makes no mention of using information from one session to the next in determining the level of restriction and instead requires diagnostic equipment and a diagnostic step that slows the process down and really may or may not lead to an effective session.

BFRBANDS.com & Occlusion Cuff

BFRBands.com produces an occlusion strap that is non-inflatable. The directions in their instructions for use call for the user to tighten the strapping to a pain scale of 7 out of 10 and don't give any indication or education around how to adjust this, or that it should even change over time. They completely ignore the idea that one level of compression is not correct from one person to another, and provide no feedback mechanism or guidance as to how to adjust their system per the individual.

OCCLUSIONCUFF.com sells a pneumatic blood pressure cuff, but again their instructions for use are very non-descript saying the pressure should be somewhere between 100-220 mmHg for arms and 150-250 mmhg for legs and should be a 7 out of 10 on an intensity scale. This further does not provide a user with feedback mechanism and guidance and further relies on subjective feedback from the user to even get close to the correct level of pressure.

Owen's Recovery Science uses a surgical tourniquet from Delfi Medical which finds an initial pressure setting by taking a limb to occlusion and then backing off by some percent. This method also is about setting an initial pressure and does not take into account prior session data or look at the outcome of a specific session in order to determine whether it was effective or not. Further, this method necessities hardware that is capable of occluding blood flow and could become unsafe if a malfunction occurs, unlike prior inventions around belt designs.

None of these systems offers a comprehensive, prescriptive (i.e. not requiring guessing from the user), and inherently safe system that utilizes continual feedback to hone in on the correct level of compression for each individual.

Overall Sato's inventions and products like BFRbands.com and OcclusionCuff.com are only concerned with providing a method to restrict flow in a safe fashion but fail to address or even discuss how to determine whether a treatment was effective or not, and how that information can be used in a feedback loop that takes advantage of past session results to affect subsequent training sessions, and even eliminate all the sensory equipment and procedures Sato and equipment such as Delfi Medical is advocating. The effect or requiring sensory equipment is evident in the sales prices for KAATSU and Owen's Recovery Science products which are in the multiple thousands of dollars vs. the applicant's inventions which are in the hundreds of dollars.

The applicant was unable to find prior inventions which utilize the applicant's invention of creating, monitoring, and adjusting a personalized blood flow restriction training program based on the efficacy of performed sessions, or even adjust during a single session based on efficacy. The applicant's invention as described herein covers multiple methods of ascertaining efficacy both automatically or via human input, and how a strategy can be implemented that leads to a safe and effective program over time. It has been observed that if users start BFR training for the first time that putting compression levels on them at the level they need to be effective can cause soreness as the body needs time to adapt, and can turn off potential users. Therefore creating a program that is comfortable and can ease someone into a workout by understanding when a session is effective, starts being effective, and optionally the degree of effectiveness can help spread adoption of the technology as it takes the thinking and expertise out of the user's hands. The applicants' inventions also address deficiency in prior methods of application of BFR.

Finally, the applicant will disclose an invention for increasing the comfort and safety of a pneumatic BFR system by pre-inflating the system to a minimal inflation level before donning the system. None of the applications or products founds employed such a tactic. KAATSU protocols call for measuring a "base pressure" but this pressure is measured while the bands are on the user, not before. By not pre-inflating the system, the user risks being able to over tension the system such that there is no volume for the air to pump into. The result is that there is very little "give" in the system and as the muscle expands, it may reach the elastic limit of the band and starts preventing muscle expansion due to contraction which is painful, and potentially could occlude blood flow.

BACKGROUND OF THE INVENTION

Objects and Advantages

Accordingly, besides the objects and advantages of an individualized blood flow restriction monitoring system for use in designing, monitoring and adjusting a BFR training program in this specification, several objects and advantages of the present invention are:

a) to provide a comfortable training experience
b) to provide a safe training experience
c) to provide an optimally effective training experience
d) to provide a cost-effective training system
e) to provide simple and quick to use training system
f) to provide a system that is built for an individual, and constantly adjusts based on efficacy feedback from one session to the next
g) to provide a system that is built for an individual, and constantly adjusts based on efficacy feedback during an on-going session.
h) To provide a method of pre-inflation of the system to optimize comfort and safety.

Still further objects and advantages will become apparent from a consideration of the ensuing description and drawings.

SUMMARY

In accordance with the present invention, one or more inflatable belts are provided for use in an individualized blood flow restriction system, the inflatable belt comprising an outer belt material and an inner belt material, coupled together in such a manner as to create an inflatable chamber, preferably air, and the inflatable belt is used to restrict blood flow in a limb of a user, wherein the initial pressure settings of the BFR system are customized to the individual based on physical parameters, and the BFR training program is monitored over time and adjusted based on efficacy feedback obtained and input into the system algorithms.

DRAWINGS-FIGURES

FIG. 1—shows an individualized blood flow restriction system, including an inflatable belt, an inflation means, a processing means, and a communication means.

Figure 2:
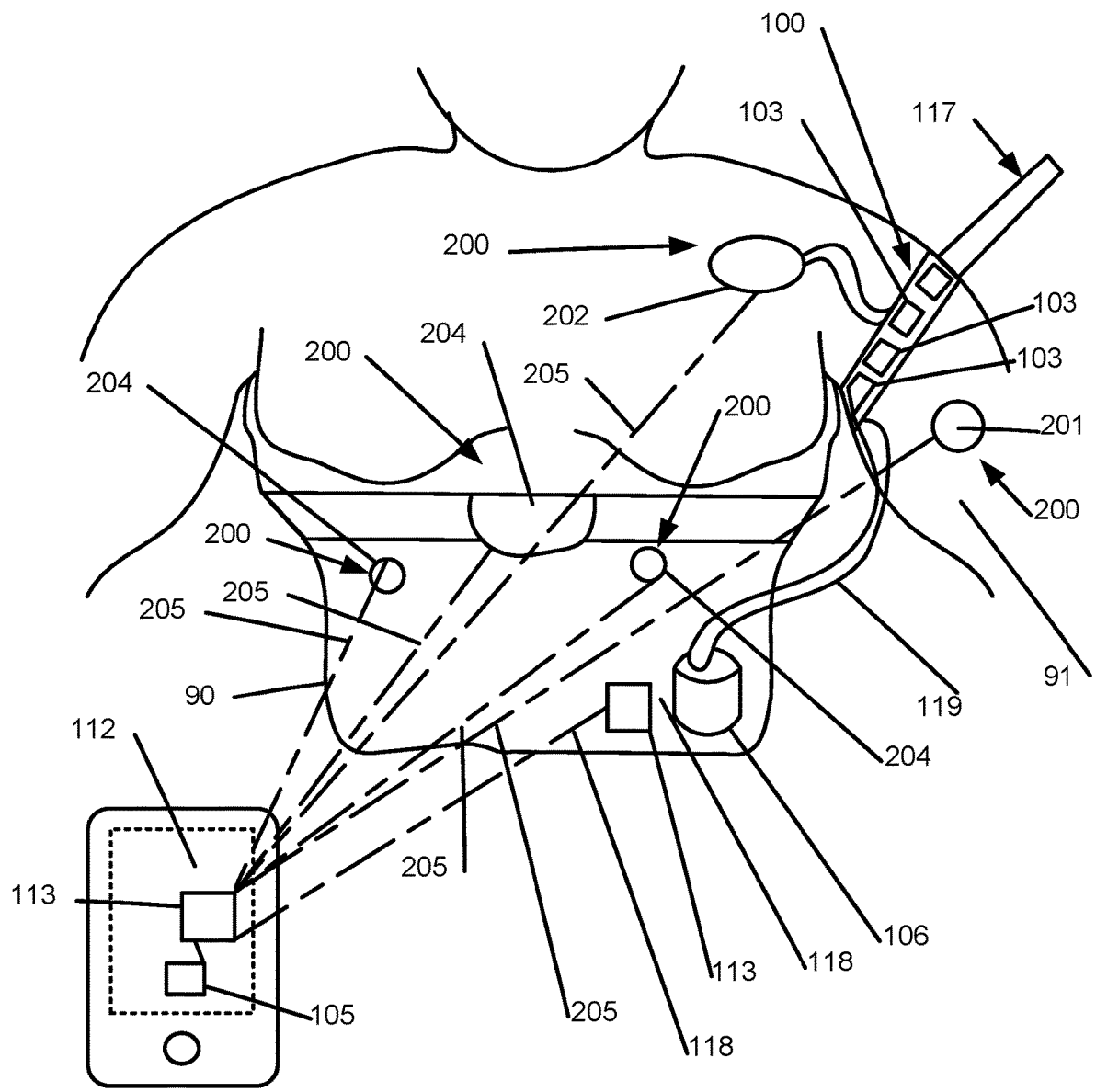

FIG. 2—shows a user of an individualized blood flow restriction system, with efficacy feedback means of varying types.

Figure 3A:
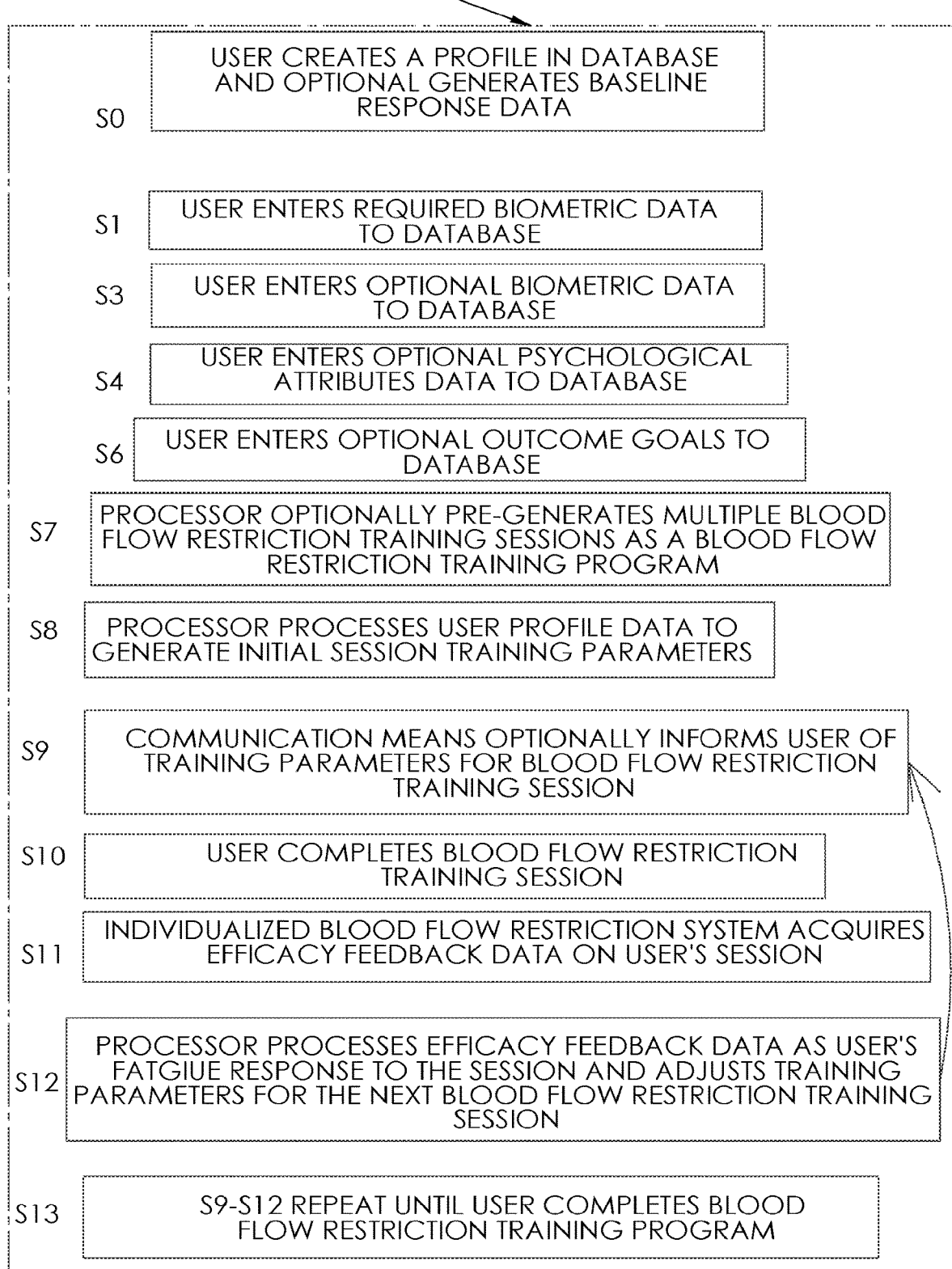

FIG. 3A—shows a blood flow restriction training program, and the steps involved to complete it.

FIG. 3B—shows a modifiable blood flow restriction training session, and the steps involved in modifying it.

Figure 4:
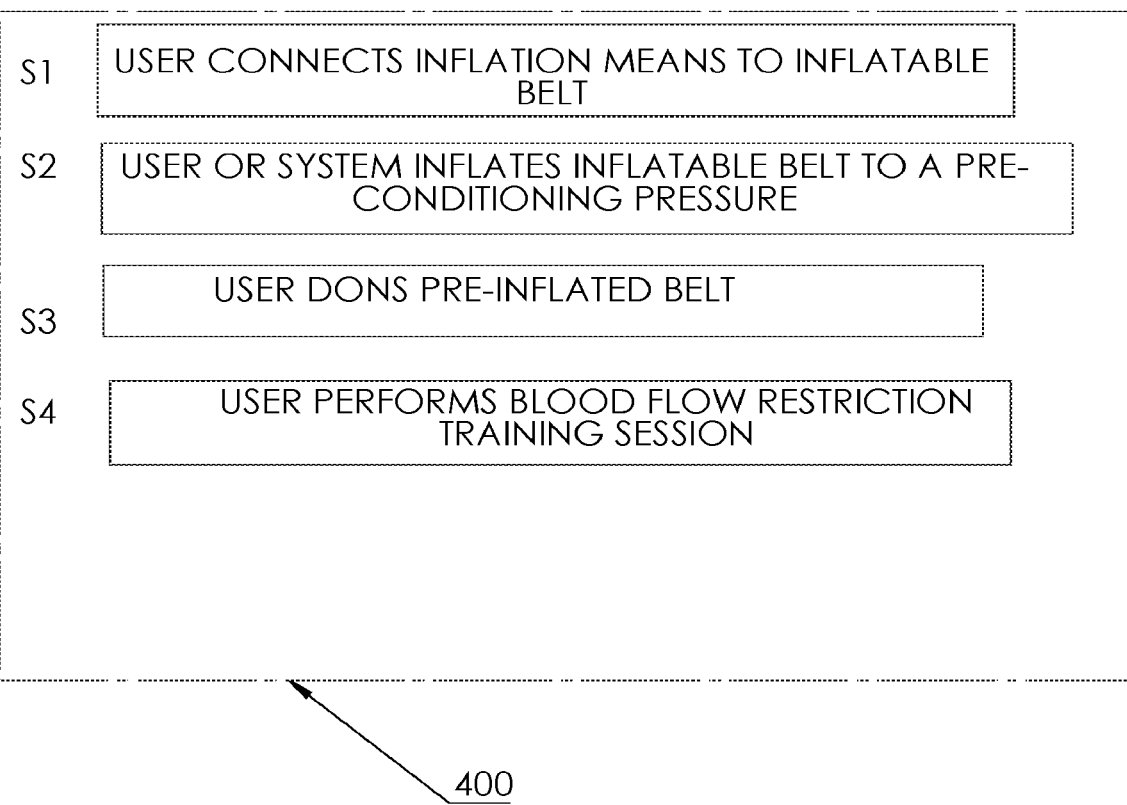

FIG. 4—shows a method of pre-conditioning a BFR belt prior to insertion on the user to improve safety and comfort.

Figure 5:
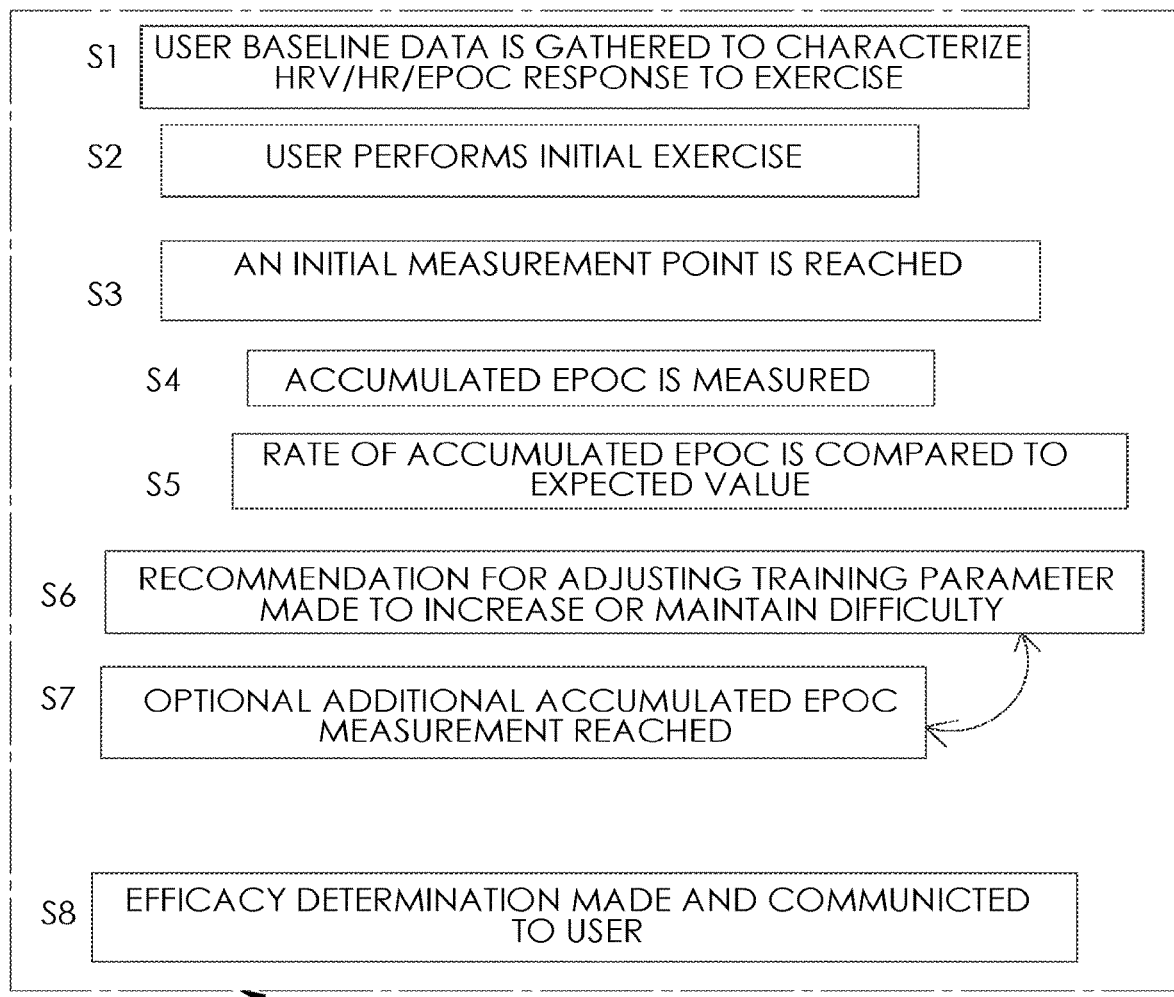

FIG. 5—shows a modifiable blood flow restriction training session and how the use of measuring a rate of change of EPOC can be used to guide the modifying of training parameters during the session.

DRAWINGS - REFERENCE NUMERALS

90 - User
91 - Extremity
100 - inflatable belt
101 - inner belt material
102 - outer belt material
103 - Inflatable chamber
104 - input port
105 - non-transitory computer readable medium
106 - inflation means
107 - belt valve
108 - gas flow shutoff means
109 - airflow
110 - first fastening means
111 - second fastening means
112 - communication means
113 - processing means
114 - inflation coupler
115 - Loop coupler
116 - individualized blood flow restriction system
117 - tension means
118 - control signal
119 - gas hose
200 - efficacy feedback means
201 - inertial repetition counting means
202 - pressure based repetition counting means
203 - communication means
204 - heart rate sensor
205 - efficacy feedback data
300 - Blood flow restriction training program
301 - Modifiable blood flow restriction training session
400 - Method of pre-conditioning a BFR belt

DETAILED DESCRIPTION

Description

A preferred embodiment of an individualized blood flow restriction system 116, including one or more inflatable belts 100 for use in the individualized blood flow restriction system is shown in FIG. 1. The inflatable belt 100 is comprised of an outer belt material 102 which may be, but is not necessarily substantially non-stretch, such as single or double side urethane coated ballistic nylon of 200 denier. The outer belt material 102 may be machine washable. The strength/weight of the fabric may be lighter or heavier, such as 50 denier or 800 denier, and lighter fabric may provide additional advantages in terms of cost, weight, and compliance for conforming to the body. Important aspects of the outer belt material are: ability to withhold a gas, or is substantially airtight, and can be connected in an airtight fashion to an inner belt material 101, forming at least one inflatable chamber 103. The connection between the outer belt material 102 and the inner belt material 101 is preferably heat sealed, or RF welded, however the reader may note that many means for attaching two fabric like materials in an airtight fashion, such as bonding or clamping, may be considered within the scope of this invention. The width of the outer belt material 102 or inner belt material 101 may be, but is not limited to, approximately 1.75-3 in for inflatable belts 100 intended for the arms and approximately 2.5-4 in for inflatable belts intended for the legs. However, the reader may note that, as described in other embodiments in previously files applications, the shape may also be non-rectangular and may span a wider or narrower region at different points around the circumference of the limb. In general, for areas where freedom of movement is needed, a narrower section may be beneficial, and for areas where a directed compressive load needs to be applied, a wider section may be beneficial. The readers shall also note that the applicants clearly understand the tradeoffs of narrower vs. wider inflatable belts 100, their effect on the pressure levels required, and effect on the inherent safety of the system. In particular, as will be described later, the applicants' preference for a narrower inflatable belt 100 enables an inherently safer system as it is much harder, and potentially impossible, with pressures normally utilized, to cut off blood flow with a narrower belt. This inherent safety factor reduces the tolerances on prescribed pressures and allows the applicant's invention to function by assuming various factors in guessing what pressures will be safe for a particular user without needing the sophisticated and complicated equipment for safety monitor discussed by Sato. However, just because the applicants refer to a preference for a narrower inflatable belt 100 does not limit the applicants' inventions around monitoring based on efficacy and other inventions disclosed herein, only to use with narrow belts.

More detail on possible configurations and concepts for creating an inflatable chamber 103 as part of an inflatable belt 100 are shown and discussed in prior provisional applications referenced in their entirety herein. Such aspects and characteristics shall not be repeated in the interest of brevity but the reader shall note that such descriptions and characteristics may be applied, but shall not limit, the characteristics of the inflatable belt 100 and components thereof, as described in this application. Similarly, while the applicants prefer a pneumatic belt, the concepts around efficacy based feedback for adjusting a BFR training session or program may also be used together with non-pneumatic belts that have some degree of measurability to them.

An input port 104 may be in communication with the inflatable chamber 103 to allow airflow 109 into and out of the chamber. The input port 104 may be an RF weldable valve component, or simply a tube welded, glued, heat sealed, or otherwise sufficiently connected in an airtight manner between the inner belt material 101 and outer belt material 102 as in an Intravenous (IV) bag. The specific material and method of fastening is not critical as long as an inlet is created in an airtight fashion. One or more valve configurations as described in previously filed and referenced provisional applications, such as a belt valve 107, may further be placed into the input port 104 as part of the inflatable belt 100, but this is not necessarily part of the assembly. As discussed in other embodiments in the previously filed provisional referenced herein, there are many such valve configurations and combinations that produce beneficial results and the inflatable belt 100 of FIG. 1 may include any one of them, or none at all. The input port 104 may be placed anywhere along the length of the inflatable belt 100 such that it is in communication with at least one inflatable chamber 103 to allow airflow 109 into the inflatable belt 100. The input port 104 is preferably located, but not limited as such, on the first inflatable chamber 103 adjacent to the loop coupler 115 as shown in FIG. 1. Many additional details have been previously disclosed and discussed in provisional applications herein and the reader is instructed to refer to, and include, all those concepts when contemplating the invention disclosed herein.

A first fastening means 110, shown as a strip of hook or loop fastener, and a second fastening means 111 depicted by a strip of mating hook or loop fastener are used to lock an outer circumference of the inflatable belt 100 when applied around a user's limb (not shown). The reader may note that many such fastening means are known in the art, and hook and loop fasteners are but one variation. Further such variations are described in previously filed and referenced provisional applications, and the reader may note these are but a few examples and shall not limit the scope of this invention. The first fastening means 110, or second fastening means 111, may in fact have itself elastic properties and serve as the function of a belt spring (described in prior applications), thereby eliminating that optional component. The first fastening means 110 is in communication with the second fastening means 111 via attachment means such as sewing or welding, and additionally in communication with the outer belt material 102, also through suitable means such as, but not limited to, sewing or RF welding. The first attachment means 110 may run along the length of the outer belt material 102, or only along a portion thereof. Guidelines regarding targeted compression range, and inflation coverage of the limb have been covered extensively in the reference previously filed provisional applications and shall not be covered further here, but shall be construed to apply as referenced herein.

A loop coupler 115 is provided at one point along the inflatable belt 100, preferably, but not limited to, one end, and the inflatable belt may be attached to the user via looping the outer belt material 102 and or inner belt material 101 over itself to capture the loop coupler as shown in FIG. 1, or may be attached with a separate material, or directly, should the loop coupler have a sew-on, or weld-on tab. The loop coupler may be any loop coupler known in the art, such as, but not limited to a metal or plastic fabric loop. The loop coupler 115 may further be constructed as a hole in the end of the outer belt material 102 and/or inner belt material 101 thereby eliminating one component. The reader shall note that many such loop couplers and means of forming a loop around a limb are known in the art and shall be considered within the scope of this invention.

Together, the first fastening means 110 and second fastening means 111 and loop coupler 115 form a tensioning means 117 for initially tensioning and locking the inflatable belt 100 in a fixed circumference. The reader shall not that the concept of tensioning a belt on a user is covered extensively in prior art and to applications to the applicants. The tension means 117 therefore may be any suitable construction that allows adjustment of tension in the object providing the compressive force to the range of muscles and may be pneumatic or non-pneumatic as shown. In the case of a simple non-pneumatic strap, the tension in the strap may be adjusted just by adjusting the strap tightness itself through ratchets, wraps, cam locks, or other means known in the art and this tension force alone may be adjust to adjust the pressure or compressive force on the range of muscles as prescribed throughout this application.

An optional body interfacing component (not shown) may be provided in communication with the inner belt material 101. The purpose, function, make-up, and design of the option body interfacing component has been covered extensively in previous applications and is referenced herein in its entirety. Additional features of an inflatable belt, such as optional stop mechanisms, edging, additional hook and loop fasteners, combinations of hook and loop fasteners, etc. have been previously disclosed in the referenced provisional applications and shall be included in their entirety when contemplating the scope of this current disclosed invention.

A belt valve 107 comprising an optional gas flow shutoff 108, may be connected to input port 104 via suitable means such as, but not limited to, gluing, friction, heat sealing, welding, etc. The belt valve 107 may be made of plastic, metal, or any other material that is suitable for holding an airtight connection and the reader shall note that many such valve styles are known in the art. An inflation coupler 114 is in communication with an inflation means 106, depicted as a palm metered bulb pump in FIG. 1 and an electromechanical pump in communication with the inflatable belt 100 in FIG. 2. The reader shall note that the inflation means may be automated, such as an electric pump, and any other means, electronic, or non-electronic, and any such mechanism that can provide a positive pressure source shall be considered an inflation means. The inflation coupler 114 may mate with the belt valve 107 to form a substantially airtight passageway between the inflatable belt 100 and the inflation means 106. The junction formed by the inflation coupler 114 and the belt valve 107 may be disconnected or permanent, and in the case of a permanent connection the reader shall note that neither the belt valve nor the inflation coupler are required for the invention to work. All such configurations of belt vales, inflation means, and inflation couplers, whether existing in plural, single, or not at all shall be considered within the scope of this invention when discussing an individualized blood flow restriction system 116.

An optional feedback mechanism is further provided comprising a processing means 113 and a communication means 112, depicted as a smartphone in FIG. 1. The processing means 113 in FIG. 1 may be inside of the smartphone as should be clear to the reader, or may alternatively be in communication with the user 90 or an inflation means 106 as shown in FIG. 2, whereby control data 118 is communicated between one or more processing means in order to adjust pressure or other training parameters. In the case multiple processing means 113 are used, calculations related to efficacy may be made on one or more of the processing means without departing from the scope of this invention. Efficacy feedback data 205 may for example be collected by a processing means 113 on the user 90 and then relayed to a processing means 113 in a smartphone and the calculations done on the processing means in the smartphone and the adjustment of a training parameter done with the processing means on the user. Control data 118 may for example be an actuation signal to turn on or turn off, a speed, or any other signal that is meant to cause a training parameter to adjust. The processing means 113 may be configured to take input data via a touchscreen shown as communication means 112. The input data may include, but is not limited to, feedback from the user via input to a touch screen on the smartphone of FIG. 1 relating to a current or completed blood flow restriction training session. The reader shall note that the applicants are using the smartphone depicted in FIG. 1 as an example, but shall generalize the concept to: getting feedback relating to the efficacy of a session, processing this feedback according to an algorithm, optionally running on the processing means 113, and subsequently altering a subsequent parameter setting of a blood flow restriction training session. The reader shall further note that while the applicants discuss altering a training parameter, should the evaluation of the parameter indicate the parameter is at an acceptable level, and decide not to change the parameter, this non-change shall also constitute "altering" of the parameter as described in this application. For example, the user 90 may enter data via a piece of paper and give to a trainer who may input the data via a keyboard acting as communication means 112 on an auxiliary computer running an algorithm on the CPU acting as processing means 113, to process the feedback data and then relay the result to a second computer, for example at the users home, via email, on how the training parameter, in this case the pressure setting, should be altered. The reader shall note that it is not necessarily important where or when efficacy feedback data 205 is collected, processed, consumed, or otherwise utilized, and all such combinations, configurations, and timeframes shall be considered within the scope and spirit of this invention. Further efficacy feedback means 200 shall be described in more detail below.

The processing means may be in communication with non-transitory computer readable medium 105, such as, but not limited to, a piece of EEPROM or flash memory, or external memory stick, and this memory function may store any of the algorithms, limits, training parameter settings, EPOC algorithms, or any other piece of software data that is required for use in carrying out the methods of the applicants' invention disclosed herein. The reader shall note that storing data, algorithms, and settings in non-volatile memory is common in the art and such common practices shall apply herein.

The efficacy feedback means 200, and feedback mechanisms as disclosed in FIG. 2 and discussed further below, may also apply to belts, straps, wraps, or other non-inflatable means of restricting blood flow in an extremity of a user without departing from the scope or spirit of this application. Such non-inflatable means may be elastic or inelastic and the reader shall note that the overall concepts around efficacy based feedback, measuring, and adjusting the individualized blood flow restriction system 116 shall not in any way be limited to inflatable blood flow restrictions means. Many such straps, wraps, and other non-inflatable means have been disclosed in various patent applications or are used in the public domain and the reader shall note that all such means for restricting blood flow in the body shall benefit by implementation of the applications inventions discussed herein regarding prescribing, monitoring, adjusting, or otherwise guiding one or more BFR training sessions based on efficacy feedback data 205.

PREFERRED EMBODIMENT

Operation

The inflatable belt 100 of FIG. 1 is applied as follows as the first part of the individualized blood flow restriction system 116. First, a user 90 selects an appropriate size of inflatable belt 100 based on their upper arm girth if exercising the upper limbs, or upper thigh girth if exercising the lower limbs. If a body interfacing component (not shown) is provided, and if the body interfacing component is detachable, the steps to get set up shall be substantially similar to those described in the previously filed provisional application referenced herein.

Optionally, a method of pre-conditioning a BFR belt 400 is shown in FIG. 4 as a means of increasing the safety and comfort of the inflatable belt 100 for the user 90. First, as shown by S1 the user connects the inflation means 114 to the inflatable belt 100 via belt valve 107, if the inflation means is not already permanently connected. Next the user 90 inflates the inflatable belt 100 to a pre-conditioning pressure S2 by activating the inflation means 114. The reader shall note that the activation of the inflation means 114 may alternatively be done automatically, for example, but not limited to, by a sensor that triggers when the inflation means is first connected to the inflatable belt 100. The reader shall further note that there are other means of determining when and how to inflate, using various actuators and/or sensors, and further the exact pressure to which the inflatable belt 100 is inflated may also be a range of pressures and not a specific pressure. All that is important is that the inflatable belt is intentionally, partially, filled prior placement on the user 90. Pre-conditioning pressures may be on the order of 20-150 mmHg, or even greater depending on the size of the belt to be used, and the reader shall note that a precise pressure range is not required and shall not limit the concept of pre-inflating the inflatable belt 100 prior to placement on the user 90. In S3 the user dons the inflatable belt 100 as described next, and performs a prescribed blood flow restriction training session S4. By pre-conditioning the inflatable belt 100 with a partial inflation, the user is improving the safety of the inflatable belt because the pressurized bladder acts as a buffer under which blood may be squeezed during muscle contraction due to the compressibility of the gas. Doppler ultrasound measurements have shown this effect that with the applicants' inflatable belt 100, the compressibility of the bladder acts as a dam, and when muscles are contracted, there is enough pressure in the blood vessels to squeeze blood past the obstruction, ensuring some amount of blood flow as a countermeasure to the risk of blood clots. Another benefit is that the inflatable belts 100, particularly when non-stretch, can be over tensioned by the user, which then leads to muscle compression and discomfort during the session. This is in fact one detriment to using non-inflatable belts for blood flow restriction. When the inflatable belt 100 is not filled with air, it acts as a normal strap or rope, and can be tightened so much that it reduces the volume of gas that can fill the inflatable chamber 103 once placed on the user 90 down to an insufficient volume. The consequence is very high chamber pressures for relatively little air volume, and thus, less expansion potential during muscle contraction and greater risk of blood flow occlusion and blood clotting. This concept was discussed in prior provisional applications referenced herein as a benefit of the squishy body interfacing component acting as a standoff. Since the time of that filing, the applicant has invented this new concept of pre-conditioning the inflatable belt 100 to achieve the described benefits. No other system recommends inflation of the belts prior to placement on the body, and this inventive step has significant consequences as to the safety and comfort of the individualized blood flow restriction system 116.

To don the inflatable belt 100, the user takes the inflatable belt, which may be held in loop form, but is not necessarily so, and slips it over their arm or leg into the desired position as described in Sato and previously filed provisional applications by authors referenced herein. Then the user pulls one end of the inflatable belt 100 until the desired tension is reached, which may be dictated by the body interfacing component 200, if provided, or by additional initial tensioning means, as described in the referenced provisional patent applications. The user then fastens the second fastening means 111, which may be hook fastener, to the first fastening means 110, which may be loop fastener, to secure the maximum circumference of the inflatable belt 100 around the limb 90. The inflatable chambers 103 encompass enough of the limb 90 as to provide the proper targeted compression. If the limb of the user 90 is small enough, the inflatable chamber 103 may overlap itself (or each other in the case of multiple inflatable chambers). Other methods of donning and tensioning a belt for BFR training have been discussed in previously filed provisional and utility applications to one or more of the applicants.

This ends the most basic description of the method of operation of the inflatable belt 100 and tensioning system designed within, which includes the construction of an inflatable belt, positioning the inflatable belt on the user 90, and preparation of the inflatable belt for inflation. For completeness, the full blood flow restriction system 116 operation will further be discussed in this preferred embodiment.

The previously filed provisional applications referenced herein, discus a myriad of combinations of valves and compressors, inflatable vs. non-inflatable belts, and manual vs. automated inflation. All such variations and combinations shall be applicable to this disclosed invention and for the sake of brevity, the only system configuration discussed will be that of a manual inflation means 106, inflation coupler 114, and belt valve 107. The belt valve 107 may employ a gas flow shutoff means 108 as described in the referenced provisional application. Where manual actions or adjustments may be made, the reader shall understand the applicants contemplate replacing such actions with automation and accompanying hardware, sensors, and circuitry and such additions shall be considered within the scope of this invention.

To the applicants' knowledge, the pressures to which an individualized blood flow restriction system 116 should be inflated have never been discussed or defined by Sato, in any prior applications, or in the literature in a prescriptive manner. Only Owen's Recovery Science equipment predetermines a pressure to apply, but is not at related to efficacy, only to safety. All current methods known either state a fixed pressure not related to a specific user, or rely on subjective user decision, or equipment measurement prior to a session to set a working pressure value. This is a very large gap as to making BFR widely adoptable as discussed in the background. The method and guidance to make the concept work effectively is essentially missing from the literature and documentation, and the concept of optimizing and evaluating individual sessions, as well as an on-going session, is never proposed or discussed. The applicants herein, shall disclose a variety of concepts for using efficacy feedback data 205 to effectively monitor and prescribe effective training parameter settings automatically to a given user as relates to the applicants' invention. One key attribute to the usability of a system, and therefore its ability to be used by a large population of uneducated users, is not requiring the users to understand detailed physiology or training techniques, or require the use of a trainer or medical professional, as Sato states as well in his applications. While Sato aims to solve this problem, Sato's disclosures relate only to safety and never mention efficacy, which is equally, or arguably, more important.

Optionally, the first step S0 is to create a profile and gather a baseline response of the user to a given exercise and/or exercise program, for example 3 sets of 30 reps of pushups. The response may be characterized by, but is not limited to, measurement over time of HRV, HR, EPOC, accumulated EPOC, and/or a training effect score. The baseline readings are preferably captured without application of BFR so that a user's normal score can be effectively measured in order to judge and make assumptions about training sessions when adding BFR. The process is considered the gathering or a baseline measurement of an exercise. The next step in setting up a blood flow restriction training program 300 as shown in FIG. 3 is to gather certain required biometric information about a user 90 in S1, such as, but not limited to, age, limb girths, general health (e.g. current medical problems, risk factors for CVD, risk factors for DVT's, AODM, HTN, etc.), fitness levels, and exercise habits. Further optional information may be gathered into a database S2, and may include biometric data S3 such as: resting heart rate and heart rate variability data, resting blood pressure, specific site $SpO_2$ and $SmO_2$, height, weight, sex, skin folds, various girths, various blood markers (e.g. lipid profile, HbA1c, glucose, insulin, etc.), oxygen consumption data ($VO_2$), strength and power data and/or psychological data S4 such as pain tolerance, comfort levels in how hard to push etc, and/or outcome data S6 such as strength improvement goals, increase or decrease in limb girthetc, and/or other data such as number of prior BFR training sessions. The reader shall note that the data examples listed are not exclusive of other datatypes, nor are they required for collection, and may be optionally collected while staying within the spirit of this invention. The reader shall also note that alternative to S1-S6, a generic minimum pressure value may simply be assumed instead of asking for all this information. Essentially, a very low pressure that is assumed to be safe for every person intended for use with the equipment could be used and the feedback mechanism started from this point. It would put most people further from their ideal settings and therefore may be less desirable, but it is an alternative to steps S1-S6. These data in S1-S6 may be gathered and processed via an algorithm, optionally processed on processing means 113, but not necessarily so, to produce one or more blood flow restriction training sessions S7, which may include initial parameter settings, altogether comprising a blood flow restriction training program 300. This training program may consist of various BFR training sessions, each session consisting of various exercises, various frequencies of these exercises in a given time period, duration of these exercises, repetition and set quantity goals for each exercise etc. The reader shall note that many such variables of training parameter settings such as: pressure, quantity of repetitions, frequency of repetitions, rest time between repetitions, quantity of exercises, quantity of sets per exercise, rate of EPOC, HRV targets, training effect targets, etc. are all adjustable and may be tuned based on information collected about a user. The reader shall further note that the examples listed and rather all such training similar types of parameters, and combinations thereof, shall be considered within the scope of this invention. The reader shall further note that creating an entire blood flow restriction training program 300 is itself an optional step, and the applicants' invention is not limited to such an action. Instead, the applicants' invention also works for a user who wants to simply do BFR training and keep track of and verify that their training is effective from one session to the next without a specific end target or quantity of sessions to complete. Therefore it is not necessary for the applicants' invention that a series of future blood flow restriction training sessions are created in advance, simply that a recent ongoing, or completed BFR training session is analyzed for efficacy at a point either during or after the that particular session in order to provide feedback in setting a training parameter for the current or a subsequent BFR training session.

Once certain required and optional biometric data are collected from the user 90 in S2-S6, or alternatively after a minimal assumed pressure is chosen, initial session training parameters may optionally be determined S8. Such initial session training parameters may include, but are not limited to the initial pressure and or belt fitting pressure or tension (in the case of an inflatable belt 100), or an initial belt tension in the case of a non-inflatable belt, initial load or weights, initial rep counts, initial sets and reps of exercises, initial exercises, a rate of EPOC target, an HRV and/or HR target etc. Other such training parameters are previously mentioned, and more than one training parameter may be determined in S8. An initial inflation pressure may range from between 50 mmHg to 400 mmHg for arms for example with generally higher pressures being required for larger limb sizes and younger, fitter individuals. An initial pressure range may range between 50-500 mmHg for legs for example with generally higher pressures being required for larger limb sizes and younger, fitter individuals. The reader shall note the applicants have demonstrated understanding of how inflatable belt 100 design influences required pressures, and these recommended pressure ranges may be adjusted down for large belt sizes or up for narrower belt sizes. The initial training parameter settings, or pressure as discussed above, may be determined as to be certain to be in a safe zone, or in other words, to undershoot for a given user, in fact to a point where the training session is not expected to be effective, but guaranteed to be safe. The applicants have determined based on experimentation on many individuals that the ranges above are safe and acceptable for initial training session parameters based on the applicants' prior inventions and designs, but exact numbers depend on a variety of factors related to each specific user. The reader shall note that while only pressure is discussed, other initial training parameters such as exercises, repetition goals, set goals, duration of session, etc. may also be prescribed at this time but are not necessarily so.

Once the initial pressure setting is determined, future pressure settings, or tension settings in the case of non-inflatable belts, may be determined based on efficacy feedback data 205. The purpose of the initial "compression" setting is to get the user 90 close, but in a safe zone that is guaranteed not to occlude blood flow and provide an uncomfortable experience to the user.

When a pressure (or tension) is determined, communication means 112, optionally informs the user 90 S9 of the training parameters prior to, and/or during the BFR training session. In the case of the manual individualized blood flow restriction training system 116 shown in FIG. 1, the user 90 then inflates the inflatable belts 100 to that training pressure. As discussed above and elaborated in prior applications and prior art, this action may alternatively be automated.

Gas, preferably air, is injected into the inflatable chambers 103 by inflation means 106 until a desired pressure is reached, causing the inflatable belt 100 to begin to restrict the blood flow in the extremity of the user 90. The pressure may be measured visually by the user, or automatically by a sensor or mechanical release valve mechanism as described in prior provisional patent applications referenced herein.

Once the desired pressure is achieved in the inflatable belt 100, the inflation coupler 114 may be disconnected (if detachable) from the belt valve 107 and the user is free to move around and do various exercises, as may or may not be prescribed in the blood flow restriction training program 300, and may or may not be communicated via communication means 112, with or without additional inflation equipment attached that adds weight, bulk, and encumbers movement.

While it is desired a user 90 follow a specific training session prescription, the reader shall note that the invention does not require this in order to provide value. Communication means 112 and processing means 113 are meant to assist the user experience and provide more direction and information to follow, requiring less thought from the user, but this is not a requirement of the invention.

When the user completes the BFR training session S10, the user then removes second fastening means 111 and pulls the inflatable belt 100, still preferably kept in loop form, off of their limb. The user may choose to deflate the belt, but it is not necessary.

Finally, the user may enter efficacy feedback data 205 into the system S11, optionally via communication means 112. As will be disclosed in alternate embodiments, the individualized blood flow restriction system 116 may alternatively gather efficacy feedback data 205 automatically during or after the BFR training session via a variety of additional means. In this preferred embodiment, communication means 112, depicted as a smartphone, may run an application that asks the user 90 to indicate the level of fatigue they experienced during their training session. The user 90 may select from a variety of levels of fatigue, for example, but not limited to: no fatigue, mild fatigue, robust fatigue, extreme fatigue. Alternatively this may be a sliding scale from 1 to 10, 1 to 100, or another means of ascertaining how tired and how much discomfort a user got during the BFR training session. The question may be accompanied by a video demonstrating the various levels or fatigue and may clearly differentiate between the levels so it is easy for a user to select to correct answer accurately. The communication means 112 may additionally ask questions about the timing of the fatigue throughout the BFR training session, or the number of completed repetitions in each set of each exercises, or this information may be gathered automatically via other sensory means such as accelerometers, cameras, etc as described later. The processing means 113 may process the data S12 to recommend a subsequent training pressure, or repetition count, or workout duration based on the efficacy feedback data provided by the user. For example, if a user enters the experience "no fatigue", the processing means 113 may calculate the next training parameter (pressure) may be the current value +20 mmHg or alternatively the current value +20%. The reader shall note the exact value may be higher, for example 50 mmHg or 50%, but shall remain less than 80 mmHg or 80% to avoid too large a step between BFR training sessions. Should the user 90 report mild fatigue, the subsequent recommendation for pressure may be +10 mmHg or 10% higher than the current session, or alternatively a range between 10-40 mmHg (or 10%-40%), but not more than 70 mmHg or 70%. If a user 90 reports robust fatigue, the subsequent training parameter for pressure may remain the same or may increase slightly, but not more than 40 mmHg or 40%. If a user reports extreme fatigue, the subsequent training pressure may be reduced by −10 mmhg or −10%, or between a range of −10 mmHg and −70 mmHg, or −10% to −70%. The reader shall note that while the pressure ranges for increasing and decreasing may vary, the important concept is that as the reported fatigue signal is increased, the degree, or amount, of increase in the training parameter (pressure in this case) relatively decreases, and in the case of extreme fatigue, the training pressure should reduce, not increase. The reader shall also note that while fatigue was used in the example above, other types of efficacy feedback data 205 as previously described, such as repetition count, may also be factored in to adjust the training parameter. For example, if a user 90 reported mild fatigue, but was not able to complete the final set of repetitions, the increase in pressure may be lower, for example +10 mmHg or 10% than if the user reported mild fatigue and also completed all required repetitions, for example +30 mmHg or 30%. This illustrates but one example and the reader shall note there are many combinations of efficacy feedback data that may influence the prescribed subsequent training parameters setting, and all such combinations shall be considered within the scope of this invention as it relates to efficacy feedback data 205 influencing current or future BFR training sessions. The steps of S9-S12 may repeat as many times as prescribed if a blood flow restriction training program 300 was created, and the reader shall recognize that these steps constitute a continuous feedback loop based on efficacy feedback data 205 that influence one or more training parameters of a BFR training session.

The reader shall note that repetitions may add further information to the calculation in that if a user 90 is unable to complete all prescribed repetitions, if so prescribed, the user may be assumed to have reached robust or extreme fatigue even without the communication means 112 requesting the user to enter their level of fatigue as previously described. Or, if the user 90 reports mild fatigue, the algorithm may assume that the user actually experienced strong fatigue and make the correct choice for the user to provide more accurate direction to the processing means 113. In the case of time duration of the session, the time of the workout duration may also impact the calculation in that if the user 90 reports robust fatigue, but the BFR training session was much shorter than anticipated, the processing means 113 may assume the user actually experienced extreme fatigue, and make a more accurate choice for the user to produce a proper recommendation for the next BFR training session. As mentioned above, sensory data can augment the decision making by processing means 113 in that number of sets completed, the number of reps, the timing repetition, and form can be automatically known and not rely on user feedback alone for determining subsequent pressure settings.

The reader shall note that while the training parameter of focus has been pressure, additional training parameters such as prescribed repetitions, prescribed number of sets or repetitions, session duration, repetition frequency within a set, etc. may all be influenced by efficacy feedback data 205 provided by the user 90 or gathered otherwise as described in the alternate embodiments.

Alternate Embodiment-#1-HRV & EPOC

FIG. 2 shows several alternate embodiments for collecting efficacy feedback data 205 depicted as a data stream (dotted line) between an efficacy feedback means 200 and processing means 113. The processing means 113 collects the efficacy feedback data 205 for processing during an on-going BFR training session as will be discussed later, or at the end of a BFR training session as discussed above in the preferred embodiment. The processing means 113 may reside on a user's smartphone as depicted or may be delivered into the system elsewhere, in a remote location, etc as described earlier. How the data gets to a processing means 113, and where that processing means 113 is located are not limiting factors to the applicants' invention. The smartphone shown is simply a convenient contemporary way to collect the efficacy feedback data 205 and manipulate it to generate adjusted training parameter settings. There may additionally be other optional processing means (not shown), for example DSPs that take raw sensor data, digitize it, encode it, and transmit it to processing means 113, therein creating a multi-layer network of processing means and communication points for manipulating raw signal data and turning it into usable efficacy feedback data 205. The reader shall understand that such networks are well known in the field and all such known configurations and structures shall be considered within the scope of this invention.

One efficacy feedback means 200 depicted in FIG. 2 shows a heart rate sensor 204 for capturing a physiological parameter about the user 90 called heart rate variability as well as heart rate itself. The reader shall note that throughout this application the terms heart rate variability, R-R' interval, and heart rate have been discussed. For the purposes of this application the heart rate sensor shall be any sensor that captures data related to heart rate such that any or all of these measurements may be calculated: heart rate variability, heart rate, R-R' interval, EPOC, accumulated EPOC, training effect, etc. The raw data that is desired to be collected is the R-R' interval, which can be used to calculate both heart rate variability and heart rate, and the heart rate variability may document whether the brain has noticed and responded to a disturbance of homeostasis in the working muscle whose blood flow has been restricted. The heart rate sensor 204 may be different than a simple heart rate monitor in that it may require EKG leads on either side of the heart that are capable of precisely measuring the time interval between heart beats, whereas basic heart rate monitors such as described in the prior art of Satoneed only count heart beats in a certain period of time and may be worn on the wrist for example. The reader shall note there are other ways of precisely obtaining the R-R' interval via optical measurements and thus not only EKG signals are required, however the readers shall note that all these measurements are different from Sato's use for monitoring HR which is purely to check if a pulse still exists for safety. For proper HRV and HR measurement based on the R-R' interval precision is required in calculating the variability in time from one beat to the next (R-R'). While construction of heart rate sensor-heart rate sensors are well known in the art, their use in determining efficacy of a BFR training session has never been employed to the applicants' knowledge. Sato discloses monitoring heart rate and pulse waves, but in so mentioning, only discussing doing so in the limb undergoing restriction. This is because Sato is only concerned with safety and ensuring blood is flowing in the limb, thus he only suggests monitoring the pulse in that limb, which he describes as "distal the band". This clearly is not addressing heart rate variability because leads are required on either side of the heart, and ideally a third lead is used, in order to get a sufficiently accurate measurement. Further these leads may be placed either distal or proximal to the band and thus not limited in location as in Sato's application.

The applicants have shown that the variability of the time interval between heart beats of the user 90 decreases (or sympathetic tone increases) as they start to feel the fatigue signals and develop muscle failure. This directly correlates to a relative variable of how hard the person is working, and whether they are getting the right signals to the brain as discussed in the introduction to effect proper strength improvements. Further, it is an objective measure of noting the brain's response to the disturbance of homeostasis in the working muscle. Monitoring the heart rate variability therefore gives a direct measure of the efficacy of the session. If the session is completed and data calculated from the the heart rate sensorheart rate sensor 204 has reported a reduced variability or increase in sympathetic tone, then this form of efficacy feedback data 205 is communicated to the processing means 113 and recorded as robust or extreme fatigue, while no change or a decrease in sympathetic tone may be taken as indication of no, or mild, fatigue, and the pressures for the next session are adjusted upward accordingly. If the signals show a low heart rate variability, too early in the session and accompanied by failure to complete the exercises then, similarly, extreme fatigue may be determined to have occurred and the pressures reduced in a subsequent session. Therefore the HRV and HR signal may be used alone, or in combination with other data collected during the BFR training session to determine how pressures for subsequent sessions should be adjusted: up, down, or remain the same. The degrees to which the pressures may increase or decrease may vary depending on the strength of the fatigue signal as communicated by the heart rate sensorheart rate sensor 204, and may or may not be combined with other factors such as time duration of the session, or completed repetitions and sets when determining the final adjustment value, if any adjustment is needed at all. In this way, a continuous feedback loop is created from one session to the next that automates the efficacy feedback data 205 collection process and gives an objective measure off of which current or future training parameters, including but not limited to pressure, may be adjusted.

Further, heart rate variability and heart rate together may be used to calculate an estimate of the accumulated EPOC for a user for a given blood flow restriction training session 301 and the EPOC score may be used to ascertain the effectiveness of a session, and further the evaluation of EPOC scores from one session to the next can be used to evaluate the efficacy of an entire blood flow restriction training program 300.

FIG. 5 shows one variation of a method for implementing efficacy feedback during a session using the heart rate sensor 204. First, a baseline measurement is preferably generated for that exercise and/or session without any BFR, similar to as discussed in relation to S0 of FIG. 3A. The baseline measurement may serve as a standard off of which responses can be compared when BFR is added to the exercise(s). Next a user performs one or more exercises with BFR in S2 while using a heart rate sensor 204 to constantly take beat to beat interval data. An initial measurement point is reached in S3 and this initial measurement point may be based on one of, but not limited to, expiration of a timer measuring time since the exercise began, a certain number of repetitions completed, a certain number of sets completed, a certain number of exercises completed, a certain HR value, etc. The initial measurement point serves as the point to where the user has been conditioned and "warmed-up" and a proper HR, HRV, and accumulated EPOC measurement value are valid. Next in S4, one or more HR, HRV and/or estimated accumulated EPOC calculations and/or measurements are performed. In S5, the rate of accumulated EPOC is measured and compared to an expected rate of increase of accumulated EPOC in that exercise for that user, based on the baseline measurements take, for the particular session that is being performed. The rate of change of accumulated EPOC is not a variable that has been looked at or used in prior art for evaluating an ongoing session to the applicants' knowledge. Additionally, generally the prior art uses EPOC as a means for monitoring for overtraining where a high accumulated EPOC means that long recovery periods are required and is thus not necessarily a good thing for the user, or is used more as a warning. In the applicants' invention however, the use is the opposite. In S6 the comparison of the rate of accumulated EPOC is used to either adjust a training parameter to increase the intensity of the workout, or to instruct the user to continue with the current training parameter settings.

For example if the rate of accumulated EPOC is lower than a pre-determined expected value at a specific checkpoint for an effective session, the user may be instructed to increase one or more of, but not limited to, the pressure in the inflatable belt 100, if the belt is inflatable, the load being used, or the frequency or repetitions. In the case the calculated rate of change of EPOC value is equal to or greater than the pre-determined expected value, the user is instructed to continue with the current settings and finish the workout. In neither case is the user instructed to stop the workout. A blood flow restriction training session 301 may comprise more than one EPOC "checkpoints" and these checkpoints may be fixed from the outset by one of but not limited to: time, completed repetitions, etc., or they may be variable based on the results of one or more previous checkpoint measurement results. For example, if a previous rate of accumulated EPOC yielded a change in at least one training parameter, a subsequent checkpoint may be made sooner than if the compared result yielded that all training parameters were appropriate. Finally in S8 an efficacy determination is made as to the effectiveness of a blood flow restriction training session 301. The result may be displayed to user or simply stored in memory or used in calculations of a blood flow restriction training program 300 as a whole. In evaluation a program as whole, a training effect score may be created for each session and the training effect scores evaluated over time to give the user a sense of whether they are on track to see the results they are expecting in the long term. This extension on FIG. 5 as to evaluation effectiveness of an entire program based on the training effect score is not shown in a flow chart, but the reader shall understand conceptually this is similar to the program and evaluation of FIG. 3B.

Heart rate drift is another phenomenon that may be observed and used to determine when the body is starting to react to a disturbance of homeostasis. Heart rate drift requires constant exercise, such as running buy may be sensed by the heart rate monitor 204 during the training session depending on the exercise prescription for that training session. Heart rate drift is manifested by an increase in heart rate without an increase in workload or intensity of the session, and if such a pattern is observed, this may be used as another indication the body is reacting to the disturbance of homeostasis, and this monitoring and measurement may be used analogous to the monitoring and observation in changes in HRV and sympathetic tone. The applicants further contemplate using heart rate drift in a non-traditional manner whereby heart rate drift is monitored for intermittent, easy, normal exercise wherein it is normally only observed in long duration constant exercise like treadmill running. The user's heart rate drift may for example be monitored from one set to the next to look for increases in heart rate where such increases are not normal to be expected, and which may further be verified by comparison to a baseline session where increases in HR were not observed.

The reader shall note that this alternate embodiment may be used for general workout routines and not only BFR. In prior art uses of accumulated EPOC, users finish their training session and then get a score as to how intense their workout was, and this score may be correlated to a training effect and suggested recovery period. However, this doesn't help a user who may be training harder than desired during a given session. Therefore, the novel and inventive idea of looking at rate of change of EPOC as a predictive mechanism may be used generally and shall apply beyond the scope of BFR training. Whereas in BFR exercise, excess damage is not a concern and thus reducing intensity is not a consideration, in the case of generic training, the rate of change of EPOC may be used to alert a user to adjust a training parameter to reduce the intensity of the training mid-session. In summary therefore, if the rate of accumulated EPOC calculated is less than a pre-determined expected value for a given point in the training session, the user is suggested to increase the intensity by adjusting a training parameter; if the rate of accumulated EPOC is comparable to a pre-determined expected value, the user is instructed to maintain training parameters; and if the rate of accumulated EPOC is more than a pre-determined expected value the user is instructed to adjust one or more training parameters to reduce the intensity of the training session. Finally, the reader shall understand that the measurement of EPOC is an estimate only, and certain tolerance bands, for example +/−5 to +/−20% may be used in the decision making. For example if a rate of change of EPOC is expected to be X, and a tolerance band for keeping training parameters the same is 0.95X<Y<1.05X then if Y, the calculated value is within this tolerance band, then the training parameters are maintained.

Alternate Embodiment-#2-Rep Counting (IMU & Pressure)

FIG. 2 also depicts two other forms of efficacy feedback means 200 that may or may not be used in conjunction with, or instead of, heart rate sensor 204. The reader shall note that multiple efficacy feedback mechanisms may be reported and data collected, and the quantity, and how they are used shall not depart from the invention of collecting efficacy feedback data 205 and evaluating the efficacy of a single BFR session, and then adjusting future training parameter settings based off that evaluation.

Repetition counting may provide additional information on whether homeostasis in the working muscle has been disturbed. Repetition counting may provide additional information about a BFR training session that can be used to evaluate the efficacy of that session and adjust training parameters as described above. Inertial repetition counting means 201 and pressure based repetition counting means 202 may be used together or alone in automating the process of counting repetitions and looking at repetition frequency. Inertial repetition counting means 201 may take the form of an IMU, or inertial motion unit that comprises one or more gyroscopes, accelerometers and/or magnetometers, or any other such device that is used to sense motion. Alternative methods of capturing motion, such as camera systems, for example the camera on a smartphone, may also be used to count repetitions. The inertial repetition counting means 201 is coupled in some way to the body. Such methods of coupling may include strapping, adhesives, embedded in garments, Velcro etc. and it shall be understood to those skilled in the art that many ways of attaching a wearable sensor of widely known and included herein. As the user 90 moves, the inertial repetition counting means 201 may look for an established pattern of movement to filter out what is an actual repetition and what is just regular movement. The user may alternatively tap the inertial motion counting means 201 after each repetition to log that repetition. The reader shall note that many such methods of analyzing motion and getting the data into the system are well known in the art, and what is important is that there is an automated way of gathering the quantity of repetitions and/or frequency of repetitions for given exercise during a BFR training session.

Frequency and quantity of repetitions may be important to quantify because the pattern and motion data can make clear whether a BFR training session was effective or not, even without HRV data. The inertial repetition counting means 201 can simultaneously measure the time between repetitions (frequency) and repetition quantity and communicate this information to the processing means 113, and the communication may happen during or after the session. The applicant has demonstrated through practical experience that a proper BFR session, with proper fatigue levels, has a pattern of the user 90 motion slowing down as the user gets the correct fatigue signals. Therefore, measuring the frequency of the repetitions at different points in the session can give more information about whether a user is experiencing the right level of fatigue. When coupled with the repetition count information, and the time elapsed from start of the workout, the individualized blood flow restriction system 116 can ascertain the strength of the failure signal indicated by sustained decrease in repetition frequency, and whether the failure has occurred too soon, too late, or not at all. These determination limits and analysis criteria may depend on the goals of the user and type of exercises involved, and the reader shall note that the specific implementation of the concepts described have a myriad of combinations and all such combinations and analysis criteria shall be considered in the scope of this invention. The location of the inertial repetition counting means 201 may be on the exercising limb, or elsewhere on the body. The only important aspect is that the location is such that the inertial repetition counting means 201 is in a position to give accurate information about the quantity and/or frequency of repetitions that have been performed.

Repetition counting means may also come in the form of pressure based repetition counting means 202. In FIG. 2, pressure based repetition counting means 202 may be in the form of a pressure sensor coupled to the inflatable belt 100. As the working muscles contract, the volume under the inflatable belt 100 tries to increase, and the pressure in the inflatable belt similarly increases. Depending on the exercise, the amount of the increase, the duration of the increase, and the rate of the increase in pressure, it can determine if a repetition was completed or if the result was simply miscellaneous body movement. The pressure sensor may be any such sensor as known to those skilled in the art and may not necessarily be coupled to the inflatable belt 100. In fact, in the case of a non-inflatable belt as disclosed previously, the pressure sensor may be made part of the belt itself, such as a tension measuring device, or may be placed under the belt, as in the case of a pressure pad. The reader shall note that may such variations are possible, and the important aspect is using a change in force due to expansion of the user's working muscles to ascertain whether a repetition has been completed. The location of the pressure based repetition counting means 202 may also be elsewhere than coupled to the inflatable belt 100 or non-inflatable belt, such as a totally separate belt that measures and looks for muscle contraction patterns by resting under the working belt.

Still other methods of repetition counting, contraction strength (EMG) monitoring, repetition frequency tracking, etc. may be employed such as video cameras and video analysis, or EMG signals, or any other form of sensor that transduces user 90 movement into digital signals that may be processed and analyzed to evaluate quantity, timing, frequency, duration, strength, and quality of repetitions and movements during a BFR training session. The reader shall note that may such options are available to those skilled in the art and all such means of gathering repetition data shall be considered within the scope of this invention.

Alternate Embodiment-#3-Continuous in Session Feedback

FIG. 3B depicts an expansion of step S10 from FIG. 3A, where a BFR training session may be modified as the session is ongoing, as a modifiable blood flow restriction training session 301. The reader shall note that prior discussions have focused around taking efficacy feedback data 205 at the end of a BFR training session in order to modify a subsequent BFR training session. However, in more granular detail, a modifiable blood flow restriction training session 301 may have its training parameters modified before the session is completed in order to further make the session even more effective. The process is described as follows:

S1 shows a processing means 113 generating user profile data to optionally generate initial training parameters for that session. The method of determination of these parameters has been discussed extensively above and the reader shall understand that in all such methods and concepts shall also apply to this alternate embodiment.

S2 shows a user 90 performing an exercise.

S3 shows efficacy feedback means 200 gathering efficacy feedback data 205, such as IMU and R-R' data, while the user is doing the exercise, or between exercises, but in all cases, BEFORE the session has ended.

S4 shows the processing means 113 evaluating the efficacy feedback data 205 for determining whether to adjust certain training parameters, and if so, how they should be adjusted. For example, HRV, repetition count, repetition frequency, resistance used, or motion data may show that the user is already starting to fatigue and form breaking down, but it is earlier in the session than desirable.

S6 shows as a reaction to the evaluation of efficacy feedback data 205, the individualized blood flow restriction system 116 may request the user 90, in the case of manual system, to reduce the pressure in the inflatable belt 100, or tension in a non-inflated belt, by some amount as determined based on evaluation of the efficacy feedback data 205. In the case of an automated system, the individualized blood flow restriction system 116 may make the adjustments automatically or a trainer or coach, may adjust training parameters on the fly. Contrarily, if evaluation of the efficacy feedback data 205 shows that the user is not experiencing any fatigue as would be expected at a certain point in the session, the system may automatically, or request a user or coach to manually, increase the pressure or tension in the belt. While pressure/tension are used in this example, any other training parameter may similarly be modified during an on-going session. For example the number of required repetitions may be increased if no fatigue is detected until the fatigue actually IS detected, or the rest periods may be shortened, or lengthened. The reader shall note these are but a few examples, and many such training parameters are available for modification and all such modifications may or may not be adjusted based on efficacy feedback data 205 and other data about the user 90 such as, but not limited to, training goals, psychological data, etc. as previously discussed.

S7 shows that the system, or user in case of a manual system, adjusts the training parameter(s) as instructed, to set the new value for the training parameter(s).

S8 shows that steps S1-S7 are repeated continuously as the session progresses and until the time limit expires. In this way a BFR training session is continuously monitored and adjusted while it is in progress to provide maximum effectiveness and efficiency to the user 90 in as real time as possible. In so doing, the user 90 is able to simply and easily follow instructions, and still achieve very safe, and very effective BFR training.

The reader shall note that the concepts for: types of efficacy feedback data 205, methods of collecting data, methods and ways evaluating data, training parameters to adjust, methods of adjustment guidelines for the training parameters, and other aspects of a BFR session or program, are similar whether the scope for monitoring, evaluating, adjusting, and prescribing is intra-session or intra-program and all discussed concepts shall apply regardless of whether these actions happen during a session or from one session to the next.

DESCRIPTION

Conclusion, Ramifications, Scope

Based on the applicants' knowledge and expertise, there are two separate conditions necessary to be met for effective BFR
1) the Disturb of Homeostasis ("D of H" for short)
2) The CNS (Central nervous system) sensing of the D of H and the CNS's reaction to the D of H (Systemic Response)

The applicant has disclosed concepts for both subjective and objective means to document those conditions for (1) D of H and (2) Systemic Response.

(1) Disturbance of Homeostasis
  a. Subjective measures of D of H include, but are not limited to:
    i. the alteration of form during an exercise or the frequency of the repetitions
    ii. questionnaires to the user or an observer, asking about incomplete repetitions, change of movement form
    iii. Rapid oscillation of working or adjacent muscle (muscle tremors).
    iv. Slowing frequency of repetitions of movement.
    v. Failure to complete prescribed repetition and set count, for example 3 sets of 30 repetitions.
  b. Objective measures of D of H include, but are not limited to sensing and measuring the subjective data via repetition counting means, cameras, EMG signals, timers etc. as discussed previously
(2) Systemic Response
  a. Subjective measures of systemic response include but are not limited to
    i. self reporting of "feelings of fatigue" or "muscle burn" by the client/practitioner
    ii. self reporting questions about sweat, elevated heart rate, breathing rate
    iii. the client/practitioner recognizing an increase in breathing, heart rate and/or sweating, out of proportion to the exercises performed.
  b. Objective measures of systemic response include, but are not limited to, robust increased sympathetic response as noted by change in R-R' data measured via heart rate variability (HRV). The documentation of the "CNS systemic response" can be objectively measured by an increase in sympathetic tone as measured by alterations in the R-R' interval (Heart Rate Variability), which normally would not occur for the easy light exercises performed. In turn, this R-R' interval data, together with heart rate are used in calculating EPOC, which can be evaluated as well to determine whether the body is reacting to the disturbance of homeostasis. Heart rate drift is another concept that the applicants have disclosed which may be used to detect a disturbance of homeostasis. The measurements of these physiological parameters and their changes relative to an expected baseline, which may or may not be taken with that specific user and set of exercises, may be done continuous to gather a spectrum of data. This data may then be compared with certain pre-determined limit values or thresholds which may be used programmatically to create an actionable message to a user as to how to adjust their training by varying one or more training parameters, or the adjustment may be done automatically if proper actuators and controllers are provided.

It is the applicants' contention that two conditions must occur to achieve an effective BFR session. First, Disturbance of Homeostasis in the exercising muscle must happen. Second, The CNS must sense that Disturbance of Homeostasis and react to it. The mechanism of getting data about both disturbance of homeostasis and the systemic response may be done objectively or subjectively, and one may be subjective while the other objective. All such mechanisms and combinations for gathering information about the BFR training session as it relates to D of H and systemic response shall be considered within the scope of this invention. The applicants have described in details various mechanisms, means, sensors, apparatus, points in time, etc. for how to collect this information and the various ways that training parameters may be affected by the results of analyzing this information, and the reader shall note that many more means of evaluating efficacy, collecting this information, and getting into an individualized blood flow restriction system 116 may be known and shall be considered within the scope of this invention.

In reading the available literature or previous patents, the applicants do not find indication from other researchers of how to make a single BFR session effective, nor markers that indicate that that session was effective, let alone using efficacy data to modify an on-going single BFR session in a practical way. All scientific publications refer to efficacy as an increase in muscle strength or size due to multiple (usually 10 or more) sessions, but this takes weeks to manifest. In this submission, the applicants describe both subjective and objective measures of (1) The Disturbance of Homeostasis that ensues in local active muscle and (2) the communication of that Disturbance of Homeostasis to the CNS and the CNS's efferent Systemic Response.

To this end, the applicants have invented and are disclosing a unique system and method for creating, monitoring, adjusting, and prescribing a BFR training program and/or session that is customized to the individual, and tracks and adjust various training parameters to ensure maximum efficiency and effectiveness for each user 90. By using efficacy as a feedback mechanism to evaluate each BFR training session, optionally even during the session, the overall BFR training program and/or session, if created, is made more efficient, effective, and relevant to the individual user. Feedback to users is important as people are inherently receptive of, and desiring immediate results. Letting someone know they are on their way to achieving their goals is a powerful motivation tool to get them to continue with their training. This is especially important when to see noticeable results a user must "stick with it" for several weeks and multiple sessions. By combining the applicants' invention with previous inflatable belt designs, and the concept of pre-conditioning the inflatable belt, the applicants have created a system that is also very safe for any user, and in this way does not need to employ all the monitoring equipment which is bulky, expensive, and cumbersome as described in Sato's applications. Further, by evaluating and monitoring efficacy, the emphasis on finding pressures as a function of occlusion level, as done in much of the research and in the case of Owens Recovery Science (i.e. % of diastolic pressure) is eliminated and the user need not measure or know their blood pressure, which can change from day to day, in order to perform safe and effective BFR training. By focusing on what really matters, efficacy, and using an inherently safer hardware design, the applicant has created the optimal system and method for executing BFR training.

Thus the reader will see that the various inventions described herein and in previously filed provisional applications provide an economical way to easily create a multifunctional, safe, inexpensive, guiding, easy to use blood flow restriction system and inflatable belt for incorporation therein.

While the above description contains specificities, these should not be construed as limitations on the scope of the invention, but rather as an exemplification of preferred embodiments thereof. Many other variations are possible.

Parameter Adjustments

The reader shall note that while pressure has primarily been discussed as the variable to be adjusted, there are other options that may alternatively be adjusted or may be adjusted after certain limits are reached. The prior art does not at all discuss how to adjust or modify various settings of the BFR training session or equipment in order to achieve effective results in a safe way, these parameters including: load used, number of repetitions, exercise selection, rep count, etc.

For example, one or more parameters may have a limit associated with that parameter and a priority to which that parameter should be adjusted before another parameter is changed. Additionally, parameters may be interrelated as to where one or more parameters reach a limit, then one or more other parameters are adjusted until a limit is reached, and then the one or more original parameters are further adjusted.

To provide an example. Starting loads, repetition count, exercise choice, etc. may all be fixed initially with only the pressure variable modified by the efficacy feedback system until a limit is reached for the pressure level. For arms this may correspond to 300 mmHg and or the legs this may correspond to a limit of 450 mmHg with the prior designs by the applicants. The reader shall note that the limits may be adjusted up or down based on belt width or hardware construction, and may be limited to 95% of systolic pressure of the user in some cases or otherwise 100 mmHg for arms and legs. If arm pressures reach the prescribed limit, then another variable, for example load may start to be increased. For bicep curls for example, load may initial be prescribed to be 0 lbs, and may be increased to 50 lbs or alternatively 25% of the users 1 repetition maximum. The limits may be adjusted to the individual or may be arbitrary. Once the load limit is reached, the repetition limit may be increased from the recommended 30 reps to 40 or 50 reps for example. The reader shall hereby understand that the concept of increasing one parameter preferentially before increasing one or more parameters may provide guidance to the user as to how to achieve an effective session in the safest manner. By increasing pressure first, preferably, the user is able to keep the loads and subsequent forces on joints and tissues low, while maintaining a safe state. The reader shall understand there are many combinations of alterations and preferences that shall fall within the scope of the applicants invention, but preferably pressure is adjusted as the first variable until it reaches a predefined limit.

The reader shall further note that the limits on parameters such as pressure may be device specific as stated above and the applicants have discussed the effect of hardware on parameters such as pressure in previous applicants related to hardware design for doing BFR training.

Belt Shapes/Sizes

For example, in the case of inflatable belt shape, the inflatable portion of the belt may be of any suitable geometry, size and shape to provide sufficient blood flow restriction as discussed above. Belts may similarly be non-inflatable, elastic, or inelastic. Belts may come in multiple lengths and widths to accommodate a range of individuals, and not necessarily minimized in the number of variations, but rather targeted toward a specific range of limb girths, or user types. It may be noted that wider cuffs have been shown to restrict flow to the same extent at lower pressures and may offer more comfort for certain applications that don't require dynamic movements. Such width variations for a specific user, such as assisting the elderly, may improve comfort while maintaining effectiveness. Belt shapes which employ enough tissue displacement to restrict venous return, such as some examples described herein, may be used, and may not necessarily cover the entire limb. All such configurations of profiles, sizes of belts, gas bladders, locations placements of such belts on the body, and bladders on belts, may be considered within the scope of this application.

Belt Materials

Various belt and blood flow restriction system designs have been described herein and in previously filed provisional patent applications, and various material constructions and configurations have likewise been disclosed. Various components being elastic, or stretch vs non-stretch, and relative degrees of elasticity have further been noted. The reader may note that for the sake of brevity, not all such combinations and material types have been discussed, but all such combinations, material properties or configurations may be considered within the scope of this invention. For example, in the case of the fastening means, cam-locks, ratchets, and hook and loop fasteners have been described or referenced, however many other such means of fastening two objects together may be used such as a high friction joint tri-glide style mechanism, glues or adhesives, ropes or knots, mechanical hooks, buttons, racks and pinions, high friction surfaces, etc may be consider encompassed within the term fastening means and this term interpreted as broadly as possible. Further, in the case of elastic members or fabrics, polyurethane coated fabrics may be substituted for PVC coated fabrics or a similar material, and urethane molds, but may be of latex rubber, or similar material. In all such cases where specific materials are called out, the readers may understand that, this specification is but one example, and as long as the general concept described is achieved, the specific material, or specific property thereof, is not a requirement of the invention.

Materials described similarly may be understood to encompass combinations of materials, varying material properties such as durometer or elastic modulus, lengths and widths, and profiles, which affect properties such as elasticity and coefficient of friction, may be considered within the scope of this invention. For example, where a material is deemed to be of a certain degree of elasticity, the reader may note that all materials have some elastic properties, and what is important is the function of the material as described herein. Further the readers may note that where a material may be discussed as elastic, a non-elastic, or non-stretch material may be combined with an elastic material to form what would be considered the original member (or visa-versa), but which is now two components and may not specifically match the description herein. However, in such cases, the readers may note that the applicant has in fact considered that materials may be combined to perform the function of the elements of the inventions described herein, but has not made all such descriptions because of the endless possible combinations possible. All such combinations yield the same result as originally disclosed that the belt spring member has some degree of elasticity. Yet another example is the reader may note that some element properties may be altered to remove various components. For example the inflatable belt may have some degree of elasticity in order to compensate for muscle contraction. Again, the reader may note that all such combinations or omissions of components, or altering of various component properties may be considered within the scope of this invention.

User

The user in the context of this application may be deemed to mean the person using the inventions described. This may be a client, patient, instructor, personal user, doctor, athletic trainer, coach, etc.

General

One skilled in the art will recognize any minor modifications that would be needed for such an intermingling and such modifications may be considered within the scope of this specification and claims. Further, it may be recognized that many of the components, processing means, sensors, etc. described may be combined into a single object or broken into multiple objects. While the applicant discusses some of these options briefly in the application, it may be recognized any and all combinations of the components and their interconnections discussed herein may be considered within the scope of this application and covered by the claims written. Similarly, it may be recognized that many components in the system and their connection points, or connection means, may also be interchanged or rearranged to achieve the same effect as the disclosed configurations. For example, where it is discussed that it may be advantageous to de-couple the inflation means from the inflatable belt, and a pressure relief valve is used to limit a maximum pressure in the belt, the pressure relief valve may reside either on the belt side of the coupling or the inflation means side of the coupling. In the case of residing on the belt side of the coupling, then no further shutoff mechanism is necessary on the belt side of the coupling. However, the invention will function substantially the same if the coupling employs a shutoff function to keep air in the belt, which is opened during connection of the inflation means, and the pressure relief valve is on the inflation means side of the coupling. In such a case, as long as the inflation means is connected, the pressure relief valve is in the same air-circuit as the belt, and limits the pressure therein. Upon disconnection however the pressure relief valve is not connected in the air-circuit of the belt, however neither is the inflation means and thus there is no risk of too high pressures accumulating in the belt. Thus the system is substantially similar in both cases. This is but one example, and in general, valves, and valve types, fastening means, such as cam locks, hook and loop fasteners, ratchet mechanisms, belt springs, inner and outer belt materials etc. may be interchanged, used in quantities of more than one, altered in width, length, or profile, employed in conjunction of overlapping belt styles, or doubling back of belt styles for locking, or more complicated belt designs such as those shown in patents to Sato, and the inventions disclosed herein may be considered to have encompassed all such permutations and combinations of such components. Yet another example is the inflatable belt may have two input ports, one to allow air in and another in communication with an outlet system such as a pressure relief valve. While such design is not shown in the figures above, the reader may note this concept is another example of how multiple items may be employed, and components shifted within the system to connect with different components, while the same overall system and effectiveness is maintained. Further still, the location and placement of various elements may be moved and altered such that they appear to differ from the figures shown, and description attached, however, all such configurations and combinations may be considered within the scope of the inventions disclosed herein. For example, in the case of the hook and loop fastener shown on the inflatable belt in FIG. 1A, the hook and loop fastener may be exchanged and the function still maintained. In addition, the location of the input port may be in the middle of the inflatable belt instead of on one end. The body interface component, such as neoprene rubber, shown in FIG. 2 may be permanently attached the inflatable bladder, or it may be removable. If removable, the attachment means may be for example, hook and loop fasteners, and the fasteners may be along the edges or may run along the full width of both the inflatable bladder and body interface component. In the case the hook and loop fasteners run along the full width, they may be elastic such that the inflatable bladder may still inflate against the user's limb. In the cases or processing means, sensors, and sensor data, the applicant shall note that sensors and processing means may be combined or split, that data may be transferred over wire, or wirelessly, that actions may be done manually, or automated, and that such actions may be initiated by the user or by the system automatically. The processing means 113 may be local to the user 90 or may be located elsewhere. There may be multiple such processing means 113 collectively referred to as the "processing means" within the intention of this application and invention, and these different processing means may run one or more algorithms or portions of algorithms, or data manipulation as part of the system's evaluation of efficacy feedback data 205 and subsequent use in adjustment of training parameters. The reader shall note that the exact network and software, and where the software is executed, is not important, but rather shall not that the spirit of the invention is that there is some form of processing capability and some form of data analysis capability within the individualized blood flow restriction system 116. The communication means 112 may be visual, audible, readable, tactile, or otherwise capable of communicating information to the user. As illustrated, there are many constructional permutations and combinations, and altering of various material properties, components, connections, algorithms, etc. which yield satisfactory results in an in an individualized blood flow restriction training system 116, and all such combinations and permutations and material property choices may be considered within the scope of this invention.

Belt Configurations

As has been discussed in both this application and patents to Sato, there are a variety of ways to form a belt around a user's limb and each has some advantages and disadvantages as discussed in the various applications. The reader may recognize that the inventive concepts disclosed herein may be considered adaptable, by changing, but limited to, the following: inflation capability, size, length, location, neighboring components, adding or removing one or more components, such as a loop coupler, material property, such as elasticity, etc. Such modifications represent numerous permutations and configurations which are too many to reasonably depict and describe herein, however the reader may understand that the applicant has thought of such reasonable applications, and may consider as such, part of the scope of this disclosed invention.

Although the description above contains many specifications, these should not be construed as limiting the scope of the invention but as merely providing illustrations of some of the presently preferred embodiments of this invention. Thus the scope of this invention should be determined by the appended claims and their legal equivalents, rather than by the examples given.

What is claimed is:

1. A method for blood flow restriction training, the method comprising:
   positioning an inflatable blood flow restriction device around a limb of a user;
   at least partially inflating the inflatable blood flow restriction device to a working pressure to reduce blood flow in the limb;
   conducting a training exercise with the inflated blood flow restriction device in place on the limb;
   capturing, via a sensor, data during the training exercise; and
   determining, based at least in part on the captured data, efficacy of the training exercise for the user.

2. The method of claim 1, wherein the blood flow restriction device comprises an inflatable chamber having a first side and a second side, wherein at least one of the first side or the second side comprises a non-stretch material.

3. The method of claim 1, wherein the sensor comprises a heart rate sensor comprising a first lead placed under the right clavicle of the user near the right shoulder and within the rib cage frame, a second lead placed under the left clavicle of the user near the left shoulder and within the rib cage frame, and a third lead placed on the left side of the user below the pectoral muscles on the lower edge of the left rib cage.

4. The method of claim 3, wherein the data comprises data regarding sympathetic tone of at least one muscle in the limb.

5. The method of claim 3, wherein the data comprises R-R' data.

6. The method of claim 5, further comprising determining, at least in part from the R-R' data, heart rate variability for the user in connection with the training exercise.

7. The method of claim 6, further comprising determining, based on the heart rate variability, efficacy of the training exercise for the user.

8. The method of claim 3, further comprising:
   receiving, from the user and in response to a prompt, user input characterizing a fatigue response of the user to the training exercise,
   wherein the determining efficacy of the training exercise is performed utilizing the captured sensor data and the user input.

9. The method of claim 8, further comprising:
   updating a future training exercise plan for the user based on the efficacy determination.

10. The method of claim 9, wherein the updating the future training exercise plan comprises modifying the working pressure of the inflatable blood flow restriction device by between 10 mmHg and 40 mmHg.

11. The method of claim 1, further comprising:
transmitting, from the sensor and to a smartphone of the user, the data;
processing, on the smartphone of the user; the data to generate an instantaneous determination of efficacy of the training exercise; and
displaying, to the user on a display of the smartphone, the instantaneous determination of efficacy.

12. The method of claim 1, further comprising:
prior to conducting the training exercise, creating a database for the user, the database comprising user information including age, limb girth, general health, fitness level, and exercise habits; and
determining, based on the user information in the database, an initial inflation pressure for the inflatable blood flow restriction device.

13. The method of claim 12, wherein the database further comprises user information including resting heart rate, resting blood pressure, blood marker data, height, weight, gender, and psychological data including user-reported pain tolerance data.

14. The method of claim 1, further comprising:
pre-inflating, prior to the positioning the inflatable blood flow restriction device around the limb of a user, the inflatable blood flow restriction device to a starting pressure greater than ambient pressure but below the working pressure.

15. The method of claim 2, wherein the inflatable blood flow restriction device is configured such that inflating the inflatable blood flow restriction device from the starting pressure to a limit pressure causes a reduction in an inner circumference of the blood flow restriction device, but inflating the inflatable blood flow restriction device above the limit pressure does not result in further reduction of the inner circumference.

16. The method of claim 15, wherein the non-stretch material prevents the inflatable chamber from expanding beyond a specified range.

17. The method of claim 16, wherein the specified range is reached at the limit pressure.

18. The method of claim 8, further comprising:
observing user performance during the training exercise to obtain observed performance data,
wherein the determining efficacy of the training exercise is performed utilizing the captured sensor data, the user input, and the observed performance data.

19. The method of claim 18, wherein the observed performance data comprises:
technical form data for the training exercise, reduced frequency of contractions in the training exercise, failure to complete an assigned number of repetitions in the training exercise, and time to complete the training exercise.

* * * * *